US012665086B2

(12) United States Patent　　　　(10) Patent No.: US 12,665,086 B2
Tsoory　　　　　　　　　　　　　　　(45) Date of Patent: Jun. 23, 2026

(54) SYSTEM, METHOD AND COMPUTER-IMPLEMENTED PLATFORM FOR PROVIDING PATIENT-RELATED INFORMATION

(71) Applicant: Liberdi Ltd., Or Akiva (IL)

(72) Inventor: Hezkiah Tsoory, Maor (IL)

(73) Assignee: Liberdi Ltd., Or Akiva (IL)

( * ) Notice: Subject to any disclaimer, the term of this patent is extended or adjusted under 35 U.S.C. 154(b) by 202 days.

(21) Appl. No.: 18/254,512

(22) PCT Filed: Nov. 25, 2021

(86) PCT No.: PCT/IB2021/060959
§ 371 (c)(1),
(2) Date: May 25, 2023

(87) PCT Pub. No.: WO2022/112985
PCT Pub. Date: Jun. 2, 2022

(65) Prior Publication Data
US 2024/0021308 A1　　Jan. 18, 2024

(30) Foreign Application Priority Data
Nov. 25, 2020　　(IL) ......................................... 278995

(51) Int. Cl.
*G16H 50/20*　　(2018.01)
*A61M 1/28*　　(2006.01)
*G16H 10/60*　　(2018.01)

(52) U.S. Cl.
CPC .............. *G16H 50/20* (2018.01); *A61M 1/28* (2013.01); *G16H 10/60* (2018.01)

(58) Field of Classification Search
None
See application file for complete search history.

(56) References Cited

U.S. PATENT DOCUMENTS

| 4,718,890 | A | 1/1988 | Peabody |
| 4,778,447 | A | 10/1988 | Velde et al. |
| | | (Continued) | |

FOREIGN PATENT DOCUMENTS

| CN | 1905907 | A | 1/2007 |
| CN | 102481444 | A | 5/2012 |
| | | (Continued) | |

OTHER PUBLICATIONS

Sandra et al., Enhancements in Anomaly Detection in Body Sensor Networks, 2019 IEEE International Conference on Computational Science and Engineering (CSE) and IEEE International Conference on Embedded and Ubiquitous Computing (EUC).*

(Continued)

*Primary Examiner* — David J Stoltenberg
(74) *Attorney, Agent, or Firm* — M&B IP Analysts, LLC

(57)　　　　　ABSTRACT

Embodiments pertain to a computer-implemented platform for providing at least one user with information associated with at least one patient undergoing dialysis treatment, using a dialysis system. In some examples, the platform comprises an I/O device configured to receive patient initial input data relating to at least one patient, the patient initial input data being descriptive of a physical characteristic of the at least one patient. In some examples, the I/O device is further configured to receive updated monitoring data of the patient, the updated monitoring data being received during a dialysis treatment of the at least one patient. The platform may further comprise an analysis engine configured to determine whether the received updated monitoring data is indicative of an anomalous parameter value of the physical characteristic or not.

20 Claims, 13 Drawing Sheets

(56) References Cited

U.S. PATENT DOCUMENTS

| | | | |
|---|---|---|---|
| 4,967,754 | A | 11/1990 | Rossi |
| 5,340,359 | A | 8/1994 | Badia |
| 5,733,503 | A | 3/1998 | Kowatsch et al. |
| 5,938,634 | A | 8/1999 | Packard |
| 7,013,928 | B2 | 3/2006 | Navis |
| 7,890,341 | B2 | 2/2011 | McNally et al. |
| 8,974,410 | B2 | 3/2015 | Miller et al. |
| 9,050,411 | B2 | 6/2015 | Kelly et al. |
| 9,050,421 | B2 | 6/2015 | Bene |
| 9,078,972 | B2 | 7/2015 | Gupta et al. |
| 10,071,202 | B2 | 9/2018 | Handler |
| 10,437,958 | B2 | 10/2019 | Daniel et al. |
| 2001/0012930 | A1 | 8/2001 | Ebner et al. |
| 2002/0123715 | A1 | 9/2002 | Sorenson et al. |
| 2003/0144647 | A1 | 7/2003 | Miyahara |
| 2006/0015015 | A1 | 1/2006 | Kawamoto et al. |
| 2008/0242947 | A1* | 10/2008 | Jung ....................... A61B 5/411 |
| | | | 600/300 |
| 2009/0054743 | A1 | 2/2009 | Stewart |
| 2009/0326513 | A1 | 12/2009 | Deutsch et al. |
| 2010/0057178 | A1 | 3/2010 | Simon |
| 2010/0249663 | A1 | 9/2010 | Nishtala |
| 2011/0054440 | A1 | 3/2011 | Lewis |
| 2013/0131574 | A1* | 5/2013 | Cosentino ............. G16H 20/40 |
| | | | 604/28 |
| 2013/0184638 | A1 | 7/2013 | Scarpaci et al. |
| 2013/0303996 | A1 | 11/2013 | Rasooly et al. |
| 2013/0345621 | A1 | 12/2013 | Cicchello et al. |
| 2014/0018727 | A1 | 1/2014 | Burbank et al. |
| 2014/0094740 | A1 | 4/2014 | Lee et al. |
| 2014/0102957 | A1 | 4/2014 | Broeker et al. |
| 2014/0194809 | A1 | 7/2014 | Plahey et al. |
| 2014/0276374 | A1 | 9/2014 | Minkus |
| 2014/0309584 | A1 | 10/2014 | Bluchel et al. |
| 2015/0005699 | A1 | 1/2015 | Burbank et al. |
| 2015/0038896 | A1 | 2/2015 | Yu et al. |
| 2015/0148776 | A1 | 5/2015 | Sobue et al. |
| 2015/0150905 | A1 | 6/2015 | Zimmeck |
| 2015/0209499 | A1 | 7/2015 | Kelly et al. |
| 2015/0238680 | A1 | 8/2015 | Kelly et al. |
| 2015/0252800 | A1 | 9/2015 | Buckberry et al. |
| 2016/0346451 | A1 | 12/2016 | Stonger et al. |
| 2017/0281847 | A1 | 10/2017 | Manda et al. |
| 2017/0319769 | A1 | 11/2017 | Wieslander et al. |
| 2018/0021500 | A1 | 1/2018 | Gerber et al. |
| 2018/0243547 | A1 | 8/2018 | Fox et al. |
| 2018/0353670 | A1 | 12/2018 | Kommala et al. |
| 2019/0087906 | A1* | 3/2019 | Fields .................... G16H 15/00 |
| 2019/0125954 | A1 | 5/2019 | Mathiot et al. |
| 2019/0217002 | A1 | 7/2019 | Urakabe |
| 2019/0268215 | A1* | 8/2019 | Tellado ............... H04L 41/0672 |
| 2019/0287668 | A1 | 9/2019 | Tiwari et al. |
| 2019/0341146 | A1 | 11/2019 | Kamen et al. |
| 2019/0381231 | A1* | 12/2019 | Tsoory ................... G16H 70/20 |
| 2020/0066415 | A1 | 2/2020 | Hettig et al. |
| 2020/0245927 | A1* | 8/2020 | Burnes .................... A61B 5/349 |
| 2021/0391069 | A1* | 12/2021 | Leinfellner ............ G16H 10/60 |

FOREIGN PATENT DOCUMENTS

| | | | |
|---|---|---|---|
| CN | 102989047 | A | 3/2013 |
| CN | 103118581 | A | 5/2013 |
| CN | 204463124 | U | 7/2015 |
| CN | 106730091 | A | 5/2017 |
| EP | 0256640 | B1 | 6/1992 |
| EP | 0368959 | B1 | 7/1992 |
| EP | 0742017 | A2 | 11/1996 |
| EP | 1108444 | A2 | 6/2001 |
| EP | 0790841 | B2 | 12/2004 |
| EP | 2682605 | A1 | 1/2014 |
| JP | S59177056 | A | 10/1984 |
| JP | S645565 | A | 1/1989 |
| JP | H0451957 | U | 5/1992 |
| JP | H0623052 | A | 2/1994 |
| JP | H09239023 | A | 9/1997 |
| JP | 2009136681 | A | 6/2009 |
| JP | 2009527343 | A | 7/2009 |
| JP | 2015061605 | A | 4/2015 |
| JP | 2020518302 | A | 6/2020 |
| WO | 9906082 | A1 | 2/1999 |
| WO | 2007140241 | A1 | 12/2007 |
| WO | 2012011975 | A1 | 1/2012 |
| WO | 2012155067 | A1 | 11/2012 |
| WO | 2015159915 | A1 | 10/2015 |
| WO | 2015173833 | A2 | 11/2015 |
| WO | 2015179824 | A1 | 11/2015 |
| WO | 2016198092 | A1 | 12/2016 |
| WO | 2018115530 | A1 | 6/2018 |

OTHER PUBLICATIONS

IL office action and search report mailed Feb. 8, 2021 for application 278995.

International Search Report for PCT/IB2021/060959, dated Feb. 2, 2022. International Bureau of WIPO.

Written Opinion of the Searching Authority for PCT/IB2021/060959, dated Feb. 2, 2022. International Bureau of WIPO.

Akbilgic O., et al., "Machine Learning to Identify Dialysis Patients at High Death Risk," Kidney International Reports, Jun. 22, 2019, vol. 4(9), pp. 1219-1229.

Extended European Search Report for European Application No. 21897288.3, mailed Apr. 16, 2024, 21 Pages.

Goodkin D. A., et al., "Association of Comorbid Conditions and Mortality in Hemodialysis Patients in Europe, Japan, and the United States the Dialysis Outcomes and Practice Patterns Study (DOPPS)," Journal of the American Society of Nephrology, Dec. 2003, vol. 14(12), pp. 3270-3277.

International Preliminary Report on Patentability of Application No. PCT/IB2021/060959 mailed Jun. 8, 2023, 6 Pages.

Japanese Office Action Application No. JP-2023-531608 dated Aug. 20, 2024.

Khan I. H., et al., "Survival on Renal Replacement Therapy in Europe: Is There a 'Centre Effect'?," Nephrol Dial Transplant, 1996, vol. 11(2), pp. 300-307.

\* cited by examiner

Example patient parameter measurement configuration screenshot

JOHN DOE

ADD EXCHANGE

Example patient parameter
measurement configuration
screenshot

| Date & Time | Statu s | Duratio n | Volume | Drain Temp | Fill Temp | Weight | BP | Pulse | Turbidity-related Value | Ultrafiltration |
|---|---|---|---|---|---|---|---|---|---|---|
| 13 Sep 2019 | Low UF | 13.0 | 2166 | 36.9 | 37.5 | | | | -32 | 166 |
| 13 Sep 2019 | | | | | | | | | | |
| 13 Sep 2019 | | | | | | | | | | |
| 12 Sep 2019 | | | | | | | | | | |
| 12 Sep 2019 | | | | | | | | | | |
| 12 Sep 2019 | | | | | | | | | | |
| 12 Sep 2019 | | | | | | | | | | |

FIG. 9

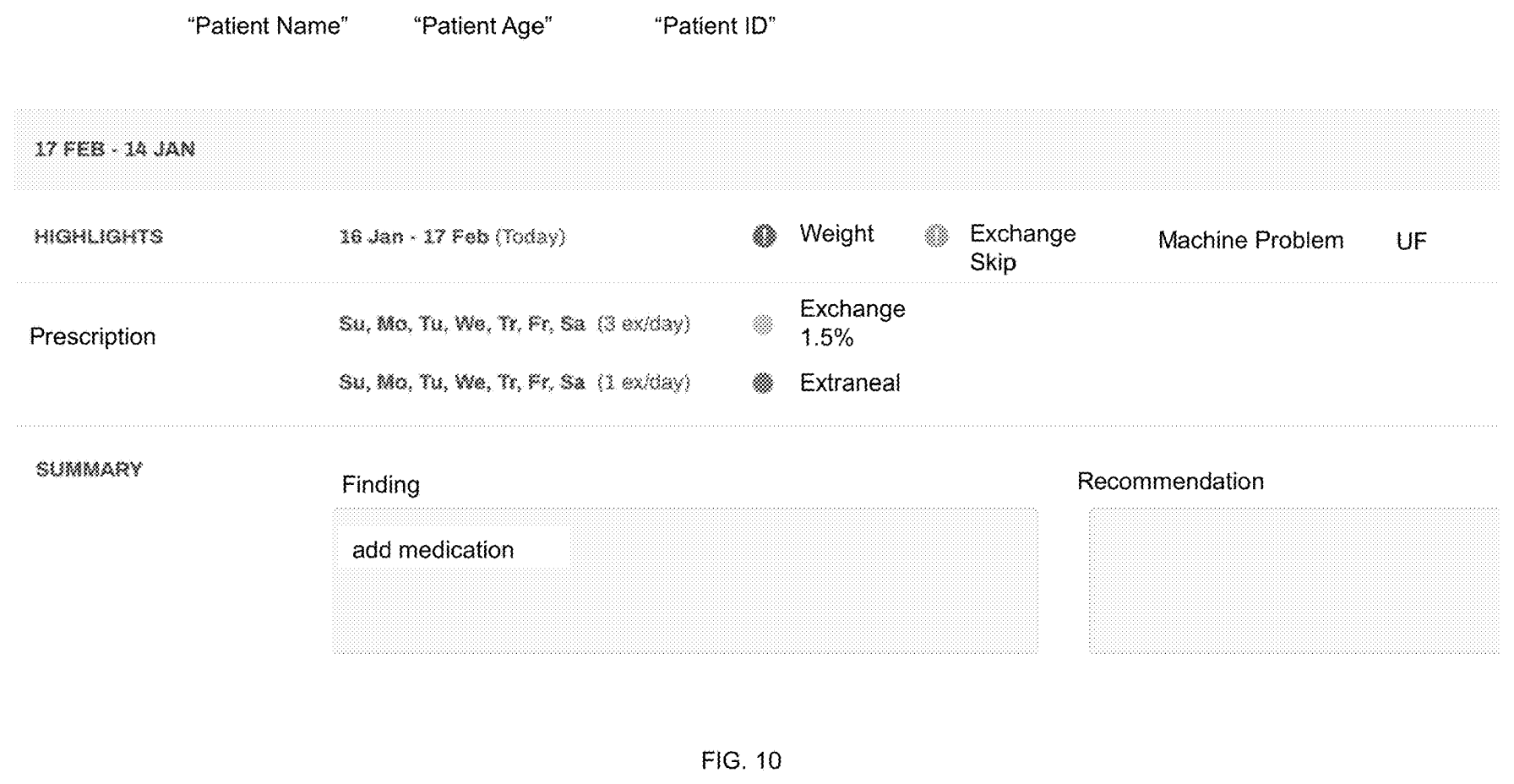

"Patient Name"    "Patient Age"    "Patient ID"

17 FEB - 14 JAN

HIGHLIGHTS

● Weight    ● Exchange    Machine Problem    UF
             Skip

16 Jan - 17 Feb (Today)

Prescription

● Exchange
   1.5%

● Extraneal

Su, Mo, Tu, We, Tr, Fr, Sa   (3 ex/day)

Su, Mo, Tu, We, Tr, Fr, Sa   (1 ex/day)

SUMMARY

Finding           Recommendation add medication

FIG. 10

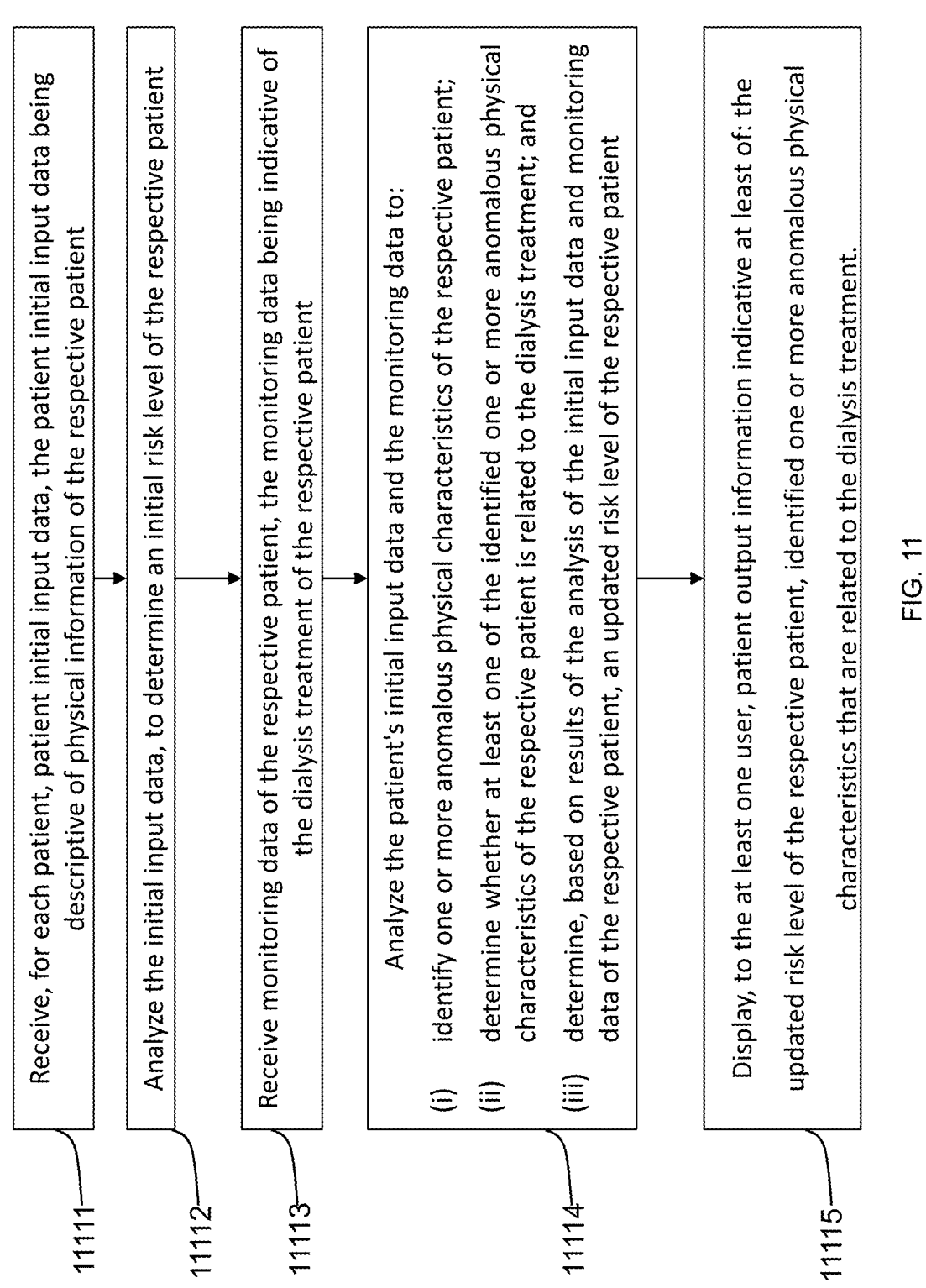

11111 — Receive, for each patient, patient initial input data, the patient initial input data being descriptive of physical information of the respective patient 11112 — Analyze the initial input data, to determine an initial risk level of the respective patient 11113 — Receive monitoring data of the respective patient, the monitoring data being indicative of the dialysis treatment of the respective patient 11114 — Analyze the patient's initial input data and the monitoring data to:

(i) identify one or more anomalous physical characteristics of the respective patient;

(ii) determine whether at least one of the identified one or more anomalous physical characteristics of the respective patient is related to the dialysis treatment; and (iii) determine, based on results of the analysis of the initial input data and monitoring data of the respective patient, an updated risk level of the respective patient 11115 — Display, to the at least one user, patient output information indicative at least of: the updated risk level of the respective patient, identified one or more anomalous physical characteristics that are related to the dialysis treatment.

FIG. 11

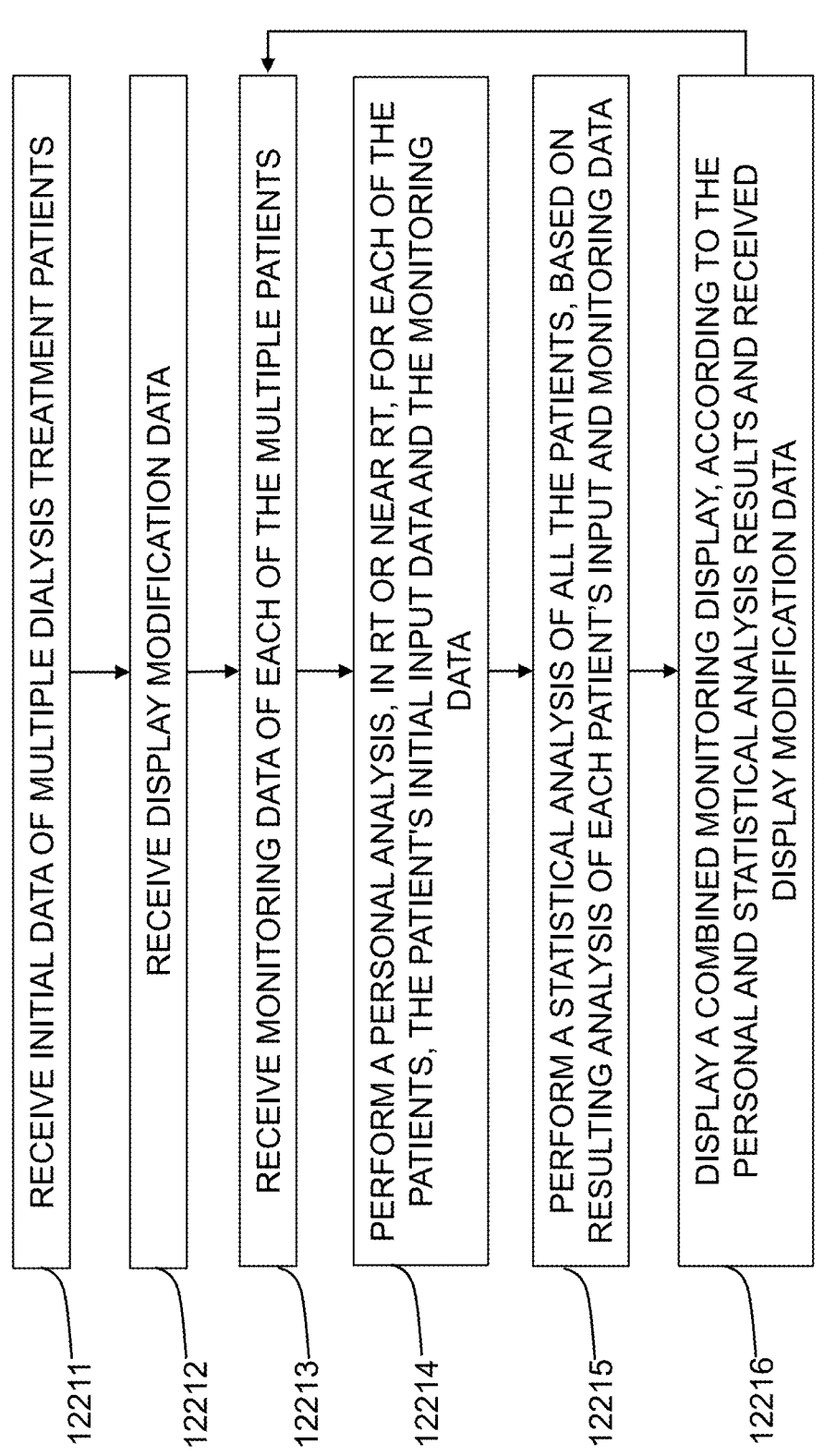

RECEIVE INITIAL DATA OF MULTIPLE DIALYSIS TREATMENT PATIENTS — 12211

RECEIVE DISPLAY MODIFICATION DATA — 12212

RECEIVE MONITORING DATA OF EACH OF THE MULTIPLE PATIENTS — 12213

PERFORM A PERSONAL ANALYSIS, IN RT OR NEAR RT, FOR EACH OF THE PATIENTS, THE PATIENT'S INITIAL INPUT DATA AND THE MONITORING DATA — 12214

PERFORM A STATISTICAL ANALYSIS OF ALL THE PATIENTS, BASED ON RESULTING ANALYSIS OF EACH PATIENT'S INPUT AND MONITORING DATA — 12215

DISPLAY A COMBINED MONITORING DISPLAY, ACCORDING TO THE PERSONAL AND STATISTICAL ANALYSIS RESULTS AND RECEIVED DISPLAY MODIFICATION DATA — 12216

FIG. 12

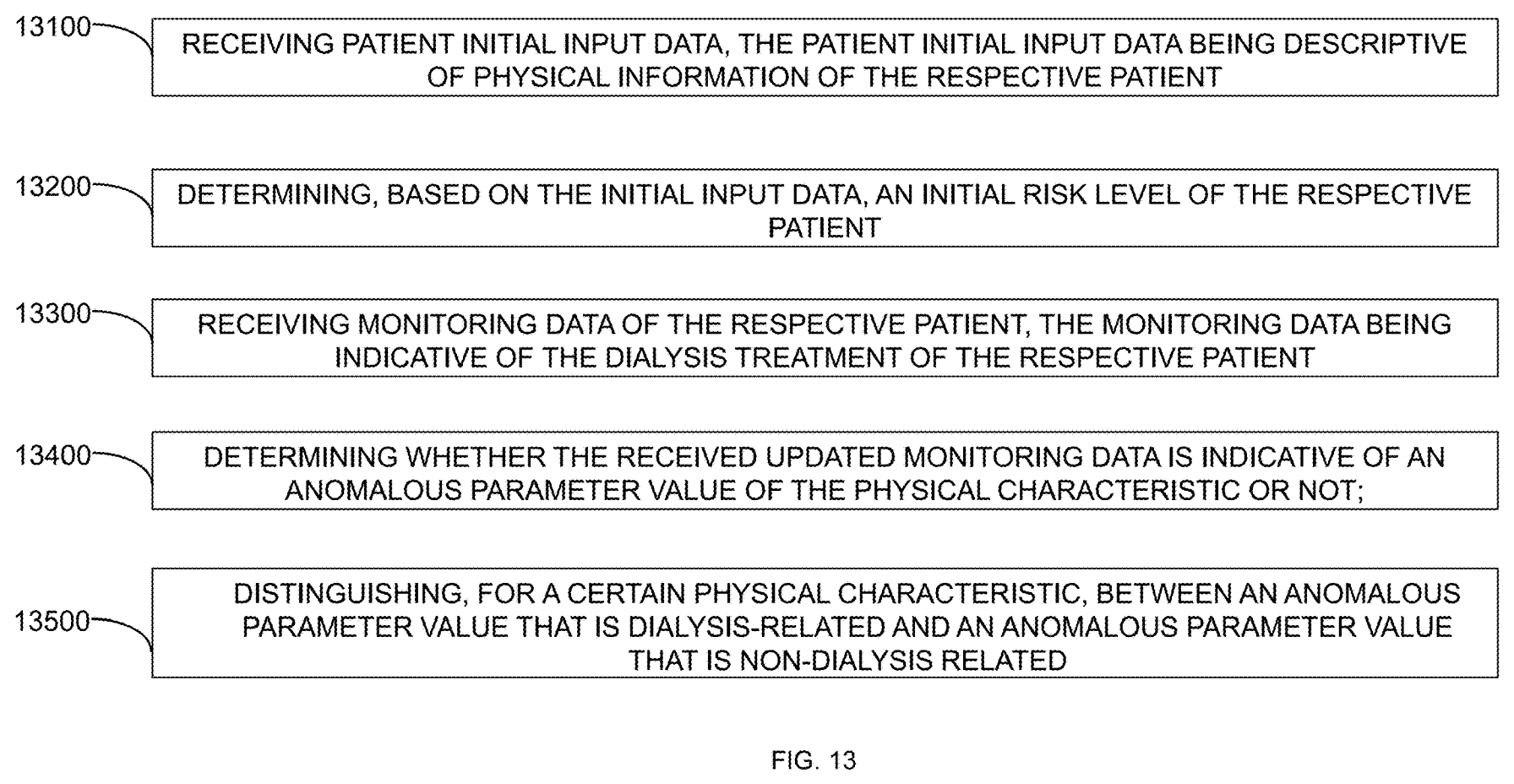

13100 — RECEIVING PATIENT INITIAL INPUT DATA, THE PATIENT INITIAL INPUT DATA BEING DESCRIPTIVE OF PHYSICAL INFORMATION OF THE RESPECTIVE PATIENT

13200 — DETERMINING, BASED ON THE INITIAL INPUT DATA, AN INITIAL RISK LEVEL OF THE RESPECTIVE PATIENT

13300 — RECEIVING MONITORING DATA OF THE RESPECTIVE PATIENT, THE MONITORING DATA BEING INDICATIVE OF THE DIALYSIS TREATMENT OF THE RESPECTIVE PATIENT

13400 — DETERMINING WHETHER THE RECEIVED UPDATED MONITORING DATA IS INDICATIVE OF AN ANOMALOUS PARAMETER VALUE OF THE PHYSICAL CHARACTERISTIC OR NOT;

13500 — DISTINGUISHING, FOR A CERTAIN PHYSICAL CHARACTERISTIC, BETWEEN AN ANOMALOUS PARAMETER VALUE THAT IS DIALYSIS-RELATED AND AN ANOMALOUS PARAMETER VALUE THAT IS NON-DIALYSIS RELATED

FIG. 13

SYSTEM, METHOD AND COMPUTER-IMPLEMENTED PLATFORM FOR PROVIDING PATIENT-RELATED INFORMATION

CLAIM OF PRIORITY

This application claims priority to Israel Patent Application 278995, filed on Nov. 25, 2020, which is incorporated by reference herein in its entirety.

BACKGROUND

Dialysis is a renal replacement treatment typically given to patients with kidney problems, such as patients with chronical kidney disease (CKD), for removing toxins and/or excess water or solutes from the patients' blood. There are several dialysis types, each using a different renal replacement method and system: hemodialysis, peritoneal dialysis, hemofiltration, hemodiafiltration and intestinal dialysis.

Peritoneal dialysis is one dialysis type, in which the patient's abdominal peritoneum membrane is used for renal replacement. In peritoneal dialysis, a fresh dialysate fluid is delivered into the patient's abdomen to create an osmotic pressure gradient across the patient's peritoneal membrane. The osmotic pressure gradient causes the transfer of excess toxins and/or water from the patient's blood stream into the fresh dialysate fluid. A catheter is brought in fluid communication with the patient's abdomen such that one catheter end is in the abdomen and the other catheter end protrudes externally from the patient's body. The external catheter end is connectable to a first container for providing the patient with fresh dialysate, or to a second container for drainage of used dialysate from the patient.

Each container is brought in fluid communication with the patient's abdomen at different time periods, where the dialysates container is first connected to insert fresh dialysate into the abdominal cavity of the patient and then, typically after some deliberate suspension period, the patient's abdomen is brought in fluid communication with the drainage container for the drainage of used dialysate.

Another type of dialysis is the hemodialysis, involving for instance an intravenous catheter, an arteriovenous fistula, or a synthetic graft.

BRIEF DESCRIPTION OF THE FIGURES

The figures illustrate generally, by way of example, but not by way of limitation, various embodiments discussed in the present document.

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. References to previously presented elements are implied without necessarily further citing the drawing or description in which they appear. The figures are listed below.

FIG. 9 shows an example table listing various treatment parameters for a selected patient.

FIG. 10 is an example screenshot of the user interface summarizing historic treatment parameters along with recommended treatments prescriptions of the past and/or future, according to some embodiments.

FIG. 11, is a flowchart of a method, schematically illustrating a process for providing one or more users with information associated with at least one patient undergoing a dialysis treatment using a dialysis system or device, according to some embodiments.

FIG. 12 is a flowchart of a method, schematically illustrating a process for providing user(s) with information associated with multiple patients undergoing dialysis treatments within overlapping treatment times, according to some embodiments.

FIG. 13 is a flowchart of a method for providing information related to dialysis treatment, according to some embodiments.

DETAILED DESCRIPTION

Figure 1:
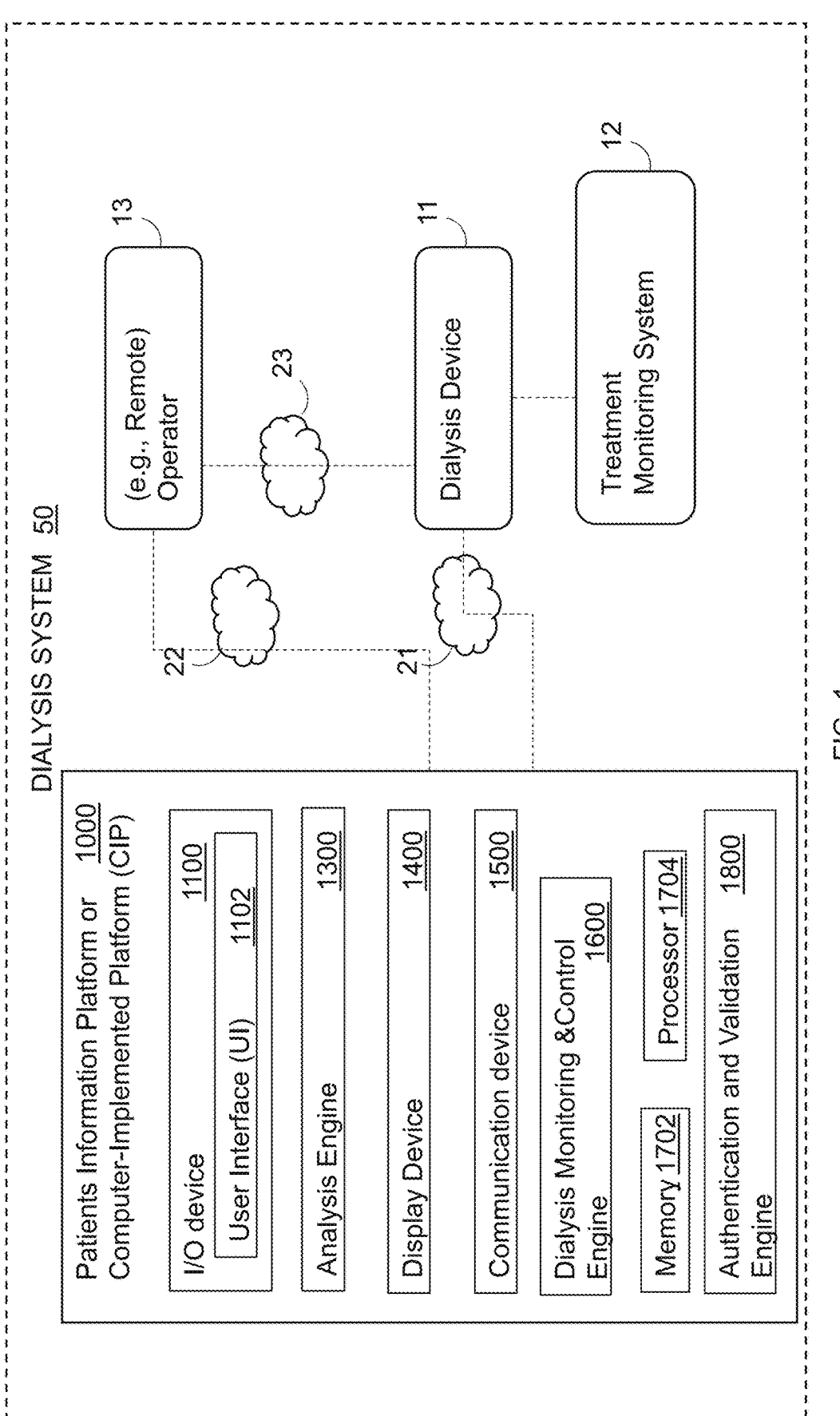
FIG. 1 is a block diagram, schematically illustrating a computer-implemented platform for providing at least one user with patients' specific physical and/or physiological information, according to some embodiments.

Aspects of embodiments pertain to computer-implemented platforms, systems and/or methods for providing at least one user, such as a professional medical user, with information associated with patients undergoing dialysis treatment, for enabling monitoring at least one patient of a plurality of patients (e.g., each patient), based on the respective patient's personal initial physical information and status and based on the respective patient's ongoing collected physical information while undergoing a dialysis treatment. The platforms and methods described herein, enable users to monitor multiple patients undergoing dialysis treatments approximately within overlapping treatment sessions times and identifying and displaying of information associated with patients showing hazardous dialysis treatment related physical characteristics in real time (RT) or near RT.

According to some embodiments, the computer-implemented platform may enable receiving, for at least one patient of a plurality of patients (e.g., each patient), patient initial input data, the patient initial input data being descriptive of information of the respective patient such as the patient's medical and/or behavioral history, updated medical tests results, patient's personal information such as patient identification details, age, weight, height, gender, phone and address, patient's caretakers details, etc.; analyzing the initial input data, to determine an initial risk level of the respective patient such as by associating the patient to one of a plurality of risk profile groups; receiving monitoring data of the respective patient, the monitoring data being indicative of the dialysis treatment of the respective patient; analyzing the patient's initial input data and the monitoring data to: identify one or more anomalous physical characteristics of the respective patient; determine whether at least one of the identified one or more anomalous physical characteristics of the respective patient is related to the dialysis treatment or not; determine, based on results of the analysis of the initial input data and monitoring data of the respective patient, an updated risk level of the respective patient; and displaying, to the at least one user, patient output information indicative at least of: the updated risk level of the respective patient, identified one or more anomalous physical characteristics that are related to the dialysis treatment.

In some embodiments, the platform may comprise a display device configured to concurrently display, to the at least one user: an updated risk level of the at least one patient, information about the associated dialysis-related anomalous physical characteristic; information about non-dialysis related anomalous physical characteristics, optionally, along with respective labels and/or other objects (e.g., tags, icons, widgets, alphanumeric symbols, audio indications) and/or by using different display modalities (e.g., different symbol colors, continuous vs. blinking), so that the user can identify which information relates to dialysis-related anomalous physical characteristic and which information relates to non-dialysis related anomalous physical characteristics.

For instance, information that relates to non-dialysis related anomalous physical characteristics may be displayed in green symbol color and/or displayed continuously and/or framed by a green frame, whereas information that relates to dialysis-related anomalous physical characteristics may blink, flash, displayed in red, and/or framed by a red frame. In some example, different audible outputs may be provided to different information.

In some embodiments, the platform may be operable to automatically distinguish or automatically differentiate (through patient data processing and/or analyzing) between dialysis-related and non-dialysis related anomalous physical characteristics, and, optionally, provide an output to indicate (e.g., to a medical professional and/or patient) which anomalous parameter value is dialysis-related and which not.

In some embodiments, the output may include annotations, labels, colors, and/or other objects and/or display modes for providing information about the dialysis-related and non-dialysis related anomalous physical characteristics.

According to some embodiments, the computer-implemented platform may be further configured to simultaneously analyze initial input data and monitoring data for a multiplicity of patients undergoing dialysis treatments, and displaying, to the at least one user, a "combined monitoring display", visually indicative of output information of multiple patients undergoing dialysis treatments.

According to some embodiments, the combined monitoring display may include visual display of one or more of the following: a table displaying information of all patients undergoing dialysis treatment, displaying, for the at least one patient of a plurality of patients (e.g., each patient), patient information indicative of at least one of: patient identification information, professional staff member associated with the respective patient, patient initial input data or part thereof, patient initial and/or updated risk level, patient one or more identified anomalous physical characteristics, patient one or more identified anomalous physical characteristics that are related to the patient's dialysis treatment; updated statistical information indicative of statistics of all patients undergoing dialysis treatment.

For example, the computer-implemented platform may be further configured to analyze initial and monitoring data of multiple patients undergoing a dialysis treatment, to generate updated statistical information indicative of one or more of: the number of patients associated with each risk profile group; the number of patients for whom one or more anomalous physical characteristics have been identified; the number of patients for whom one or more anomalous physical characteristics relating to their dialysis treatment have been identified. The updated statistical information may be displayable as part of the combined monitoring display in a visual manner e.g. through a pie chart display, bar chart display, numbers display indicative of actual number of patients in each risk profile group, histogram display, etc.

The computer-implemented platforms, systems and/or methods may be configured to receive the monitoring data of the at least one patient of a plurality of patients (e.g., each patient) via one or more measuring devices e.g. measuring devices embedded in the dialysis system. For example, the monitoring data may be indicative of operational functioning of the dialysis system being used and/or physical condition of the respective patient.

According to some embodiments, the one or more measuring devices may be configured to detect one or more dialysis parameters values associated with the dialysis treatment of the at least one patient of a plurality of patients (e.g., each patient) in real time (RT) or near real time (NRT) and transmit the measured parameters values to the computer implemented platform or system in RT or near RT. For example, at least some of the measuring devices may be embedded in the dialysis system and configured to detect dialysis system operational parameters values, in order to detect dialysis system related impediments such as undesired catheter displacement, improper catheter placement, leakage and/or blockage, dialysis system pump malfunction, dialysate turbidity state, etc. Other measuring devices may be used to directly measure the patient's physical condition during the patient's dialysis treatment session, such as the patient's RT or near RT body temperature, blood pressure, pulse, oxygen saturation level, etc. The data from the measuring devices may be received at the computer-implemented platform to be analyzed and displayed to the one or more professional users monitoring the respective patient.

According to some embodiments, data collected at each dialysis treatment session for the at least one patient of a plurality of patients (e.g., each patient) may be stored for future analysis.

According to some embodiments, the identification of the one or more anomalous physical characteristics, may be carried out by comparing at least some of the initial input data with the monitoring data of the respective patient and/or by comparing at least some of the monitoring data of the patient to one or more thresholds defining a normal and abnormal physical state. For example, physical characteristics of the patient such as blood pressure or body temperature may be measured right before the patient is to undergo the dialysis treatment and taken as part of the patient's initial input data, and those same measures may be measured during the treatment session to be compared both with the initial values thereof and with normal-range values. If the patient's body temperature is identified as rising during the dialysis treatment session, the analysis engine (e.g., analysis circuit) may associate this rise as related to the dialysis treatment, providing a distinctive display indication for an anomality related to the dialysis treatment.

According to some embodiments, the computer-implemented platform may further be configured to determine or identify a "hazardous state" of the patient, optionally where the hazardous state being indicative of related to one or more possible dialysis treatment complications. The hazardous state identification or determination may be based on the identified one or more anomalous physical characteristics. The computer-implemented platform may further be configured to display a distinctive "alarm display" when a hazardous state is determined.

The one or more dialysis treatment complications may include, for example, one of the following: peritonitis, dehydration, insufficient ultrafiltration, infection, inflammation, one or more dialysis system/device operation impediments such as undesired catheter dislocation, catheter blockage or leakage, anomalous dialysate delivery or drainage flow rate etc.

According to some embodiments, the computer-implemented platform may further include a dialysis control engine (e.g., implemented by one or more circuits or controllers) configured to automatically control operation of the dialysis system/device, based on results of analysis of the initial input data and the monitoring data of the patient.

The platforms, systems and methods provided herein may be suitable and/or adaptable to any type of dialysis treatment, using any known type of dialysis system and/or devices, such as peritoneal dialysis and/or hemodialysis.

According to some embodiments, the determination of the updated risk level of the patient may include deciding to change (e.g. increase) the patient's risk level only upon identification of anomalous physical characteristics that are directly related to the dialysis treatment that the respective patient undergoes. For example, a patient associated with an initial low-risk profile group may remain in an updated low-risk profile group if the patient's identified anomalous physical characteristics are not related to the dialysis treatment.

According to some embodiments, the computer-implemented platform may provide a medical professional user with "Virtual", "computer-implemented" or "Digital" Dialysis Center capabilities, allowing the professional user to treat many patients from a same single platform. The patients may be located at different locations (e.g., at different addresses, different medical centers in which a patient may undergo treatment, etc.). The computer-implemented platform may have a suitable user interface (UI) allowing the medical professional user to remotely select, monitor and/or control dialysis treatment for a plurality of patients in a manual and/or automatic manner.

According to some embodiments, the computer-implemented platform may be implementable via software and/or hardware units such as via a software program, a website, a control box/panel, or any combination thereof.

In order to provide a patient with improved or optimal medical diagnosis and treatment, a professional medical person such as the patient's physician is required to consider multiple patient physical related parameters such as patient's general physical parameters such as weight, gender, height, age, medical and/or behavioral history of the respective patient, insurer, type of insurance, medical insurance coverage, etc., as well as physiological parameters including, for example, up-to-date blood tests such as blood count, medical imaging data, patient parameters indicative of infections (e.g., viral) infections, a type of viral infection (e.g., indication if infection is related to SARS Coronavirus species or not), cough, breathing difficulties, inflammation, (e.g., derived from urine tests), blood pressure, pulse, used dialysate temperature, used dialysate turbidity, and/or body temperature, which are being monitored during and/or in connection with (e.g., before and/or after) a dialysis session.

In some embodiments, a patient treatment may be selected from a plurality of treatment options, and/or patient treatment parameter values may be adapted based on measured treatment parameter values and indicator values. For example, a patient treatment may be selected and/or patient treatment parameter values may be adapted based body temperature measurements (e.g., used dialysate temperature, abdominal fluid temperature, used dialysate turbidity value). To simplify the discussion that follows, the expression "physical and/or physiological patient parameter", as well as other patient-related information (e.g., social security number, name, work address, home address, phone number, email address, etc.) may be herein be referred to as "patient parameters".

In some embodiments, a medical professional user may enter (e.g., select) system operating parameters, which can include device operating parameters and/or patient parameters). For instance, an operator may manually enter treatment parameter values and, based on the manually entered treatment parameter values, a control engine may perform and control treatment of a patient.

Furthermore, various system operating parameters may be measured and, optionally, output for display to, e.g., a medical professional and/or user of the system and/or as feedback for manual, semi-automated and/or automated control purposes system. It is noted that the term "display" may include, for instance, "visual" and/or "auditory display".

It is noted that the system operating parameters may in some embodiments pertain only to the patient being treated, and in some other embodiments also to parameters relating to other patients. Optionally, the system parameters of a selected patient may be controlled based on the system parameters pertaining to a plurality of other patients. Optionally, the system parameters of a selected patient may be controlled based on the system parameters pertaining to a plurality of other patients as well as based on the system parameters of the selected patient, for example, to implement artificial intelligence (e.g., machine learning) functionalities.

In some embodiments, the system parameters may be adaptively optimized "on-the-go" during treatment such to obtain a therapeutic target outcome, defined for instance by patient parameter target values of one or more patients. For example, the system parameters may be automatically controlled to converge to the patient parameter target values. Optionally, the patient parameter target values may be defined by one or more open-ended or closed ranges, confined by upper and/or lower limits. In some embodiments, patient parameter target values may be manually adjusted by an operator, for example, by actionably engaging symbology displayed on a touch screen, to change a displayed shape and/or position of the symbology. For example, a graph or plot indicative of a target value may be adjusted by changing its shape and/or position relative to its coordinate system, by adjusting chart characteristics (e.g., by changing a bar height and/or the boundaries of a pie chart through engagement of displayed chart areas and/or chart boundaries). For example, a pie chart may be representative of a plurality of different treatment protocols that can be applied to a corresponding plurality of groups of patients. Considering for example a pool of 100 patients, the symbology (e.g. chart) may be adjusted apply a first treatment protocol a group of 60 patients, and a second treatment protocol to a group of 40 patients. The corresponding chart values may be displayed and, optionally, updated in real time, responsive to operator-initiated adjustment of the symbology (e.g., chart) characteristics.

In some embodiments, patient parameter target values for one or more patients may be entered manually by an operator. In some embodiments, patient parameter target values may be prestored in the dialysis system. Based on patient parameters and available device parameters, the operator may make a selection from a plurality of suggested patient parameter target values and/or treatment options.

In some embodiments, the dialysis system may function as a decision-support system allowing a medical professional, assisting the medical professional to select treatment parameters which are personalized to a patient, e.g., to optimize the treatment to a patient's particular needs. Personalization of the patient's treatment may be based on patient parameters and/or device parameters, e.g., processed, stored, retrieved, obtained and/or otherwise entered by a processor and/or memory of the dialysis system.

In some embodiments, treatment recommendations and/or treatment protocols may be location-based and/or insurance-dependent and/or depend on the health maintenance operator (HMO) providing the treatment. For example, the platform may receive information about a patient's location (e.g., through GPS-tracking); insurance coverage; insurance company; HMO; hospital; clinic, etc. and, based on any of the aforementioned information, alone or in any combination, recommend or apply a patient treatment.

In some embodiments, the platform may receive from patients and medical professionals information relating to the level of service (e.g., patients may provide clinic ratings), patient satisfaction, clinic appurtenances, clinic, cleanliness and/or the like; and also be operable to provide such information to patients and/or medical professionals. Patients may use such information to select from various clinics, and medical professionals or clinic managers may use such information as feedback to assess the level of service provided to patients and/or to learn on what has to be approved to improve their rating.

The term "processor", as used herein, may additionally or alternatively refer to a controller. A processor may be implemented by various types of processor devices and/or processor architectures including, for example, embedded processors, communication processors, graphics processing unit (GPU)-accelerated computing, soft-core processors and/or general-purpose processors.

The term "memory", as used herein, may include transactional memory and/or long-term storage memory facilities and may function as file storage, document storage, program storage, or as a working memory. The latter may for example be in the form of a static random access memory (SRAM), dynamic random access memory (DRAM), read-only memory (ROM), cache and/or flash memory. As working memory, the memory may, for example, including, e.g., temporally-based and/or non-temporally based instructions. As long-term memory, the memory may for example include a volatile or non-volatile computer storage medium, a hard disk drive, a solid state drive, a magnetic storage medium, a flash memory and/or other storage facility. A hardware memory facility may for example store a fixed information set (e.g., software code) including, but not limited to, a file, program, application, source code, object code, data, and/or the like.

In some embodiments, the computer-implemented platform may be configured to display a series of questions to the patient and/or the medical professional user for producing at least some of the initial input data of the respective patient. The answers provided may be used as a basis for selecting personalized patient treatment parameters and/or for determining a patient's initial risk level for suffering from dialysis treatment complications.

In some embodiments, the computer-implemented platform may be operable to determine, based on measuring values relating to operating system parameters, a level of adherence of a patient to undergo or undergoing a recommended treatment regime. For example, for at least one patient of a plurality of patients (e.g., each patient being monitored), the dialysis system may store event logs relating to the patient's treatment and compare it with the recommended treatment regime. In case of a discrepancy between the event logs and the recommended treatment, a corresponding message is output to the patient and/or medical professional, indicated for instance as an "exchange skip". Optionally, the dialysis system may be operable to automatically adapt or suggest an alternative treatment regime in case such discrepancy is detected.

In some embodiments, the dialysis system and/or dialysis device may automatically send reminders to the patient prior to a scheduled treatment. In some embodiments, the dialysis system may request the patient to approve receipt of the reminder. In some embodiments, sensors (e.g., proximity sensors, light sensors, etc.) may be employed in operable conjunction with the dialysis catheter to automatically determine whether the catheter is in fluid communication (properly connected) with the patient's peritoneal cavity to allow performing peritoneal dialysis. An output indicating that the catheter is in fluid communication with the patient's peritoneal cavity may be logged by the dialysis system. Optionally, a peritoneal fill cycle cannot be initiated from the platform (comprising for instance a suitable user interface), unless the output is received at the dialysis system (e.g., at a dialysis control engine of the system) indicating that the catheter is in fluid communication with the patient's peritoneal cavity.

In some embodiments, patient parameters may be considered for suggesting a treatment regime to increase likelihood of patient adherence. For example, the patient's age; profession; family situation (e.g., living alone or with spouse); travel itinerary; home address; work address; etc., may be taking into consideration when suggesting a treatment. For instance, a patient's travel itinerary may be stored in the dialysis system, and the treatment plan selected to meet the constraints imposed by the patient's travel itinerary.

In some embodiments, the patient information platform of the dialysis system may be operable to display information using a variety of UI display modalities. The UI display modalities may be selected and/or altered manually, automatically, or semi-automatically. For example, a display modality may be selected from a dropdown list.

In one display modality, mainly or only information relating to a specific patient is displayed.

In another display modality, information relating to a plurality of patients is displayed.

In a further display modality, information relating to a specific patient is displayed alongside comparative system parameters indicators with respect to other patients.

In some embodiments, display of patient information may be grouped according to a variety of system and/or patient parameters or criteria. For example, patients information may be displayed in groups according to their gender, age, height, race and/or weight; risk level (e.g., low, middle, and high-risk patients); co-existing diseases or medical conditions (e.g., diabetes, respiratory disorders, heart diseases or conditions, high blood pressure, patients with weakened immune system); treatment regime; medical examination results and/or diagnosis such as patient's blood, urine and/or feces test results; and/or medical examination results such as anatomic and/or physiologic imaging or diagnosis deduced therefrom, or any other non-invasive or invasive examination results such as endoscopic examination results, and/or the like.

In some embodiments, the dialysis system and/or the computer-implemented platform may identify and automatically group the patient information into risk profile groups. Optionally, patient information may be displayed according to risk profile groups.

In some embodiments, patient as well as other system-related information may be displayed according to one or more filters, which may be based on system operating parameters. Optionally, filter preferences for including and/or or excluding and/or sorting patient information may be selected. Filters may be selected using, for instance, a dropdown list, checkboxes, drag-and-drop symbols, radio buttons, "on/off" symbol, etc.

In some embodiments, filters may be ranked according to information filter preferences (e.g., primary, secondary, and tertiary filter preference). For instance, a primary filter for displaying patient information according to high-level risk profile groups may be selected, and a secondary filter, subordinate to the primary filter, may pertain to displaying patient information of patients with diabetes, for example.

In some embodiments, one or more filters may be input to the dialysis system for controlling dialysis system operating parameters. For example, a filter may define which patient parameters are included and which patient parameters are excluded from consideration by a controller during patient treatment.

In some embodiments, the computer-implemented platform may automatically suggest filters, sorting, display modalities (e.g., pivot, coloring, symbology, table display, chart display, histograms, etc.) and/or other configurable user interface options for displaying system information to select, monitor and/or control treatment of a certain patient and/or a group of patients.

In some embodiments, based on received and analyzed patients' input data and monitoring data, the dialysis system may determine and suggest one or more parameter filter configurations. A plurality of suggested filter and/or sorting options may be displayed alongside respective ranking indication (e.g., "high preference filter configuration", "medium preference filter configuration", "low preference filter configuration").

In some embodiments, the user interface may allow customizing a standard of care, and to compare between outcomes of different standards of care.

System operating parameters may include, for example, upper and/or lower limit values, and/or desired outcome values, and/or desired range values pertaining to patient and/or device parameters. For example, device operating parameters may pertain to a type of dialysate fluid; abdominal fill volume; abdominal fresh dialysate fill frequency; abdominal fresh fill start time; abdominal fresh fill end time; abdominal fresh fill flow rate; treatment protocol; treatment protocol sequence; treatment protocol preference (e.g., first line treatment protocol; second line treatment protocol, etc.); UI display modality; inflammation and/or infection-related parameter value (e.g., abdominal temperature and/or used dialysate turbidity value); dehydration-related parameter values (e.g., blood pressure); difference between a drain volume of a certain dialysis cycle and a fill volume for a later dialysis cycle, for example, to determine an ultrafiltration value. The later dialysis cycle may be measured with respect to cycle which was scheduled to start or end 24 hours after start or end of the certain dialysis cycle.

System parameter values may be measured with respect to absolute values, relative values, and/or a rate of change with respect to two related system parameter values. For example, a patient's gain in weight from a reference weight may be measured, as well as a patient's rate of gaining weight within a certain time period. Limits may be defined with respect to absolute values, relative values, and/or rates of change.

The ultrafiltration parameter value may reflect the volume difference between the previous fill and the drained volume in the current exchange. A comparatively low ultrafiltration value may be an indication of insufficient fluid removal into the peritoneal dialysis solution. Ultrafiltration can be increased by increasing the relative amount of an osmotic agent (e.g., dextrose) in the peritoneal dialysis solution. In some examples, the analysis engine may monitor the ultrafiltration parameter value to determine whether the ultrafiltration parameter value meets an ultrafiltration criterion. If the ultrafiltration criterion is not met (e.g., the ultrafiltration parameter value is below a certain low volume threshold), the analysis engine may provide an output to the peritoneal dialysis system to adapt (e.g., increase) the relative amount of the osmotic agent in the peritoneal dialysis solution to increase ultrafiltration.

The dialysis system may be operable to automatically determine device parameter values such as, for example, a type of osmotic agent and/or concentration and/or fill volume and/or dwell time value required for the at least one patient. In one example, the device parameter values may be determined prior to initiation of a peritoneal treatment cycle. In a further example, device parameter values such as osmotic agent concentration may be automatically adapted during a peritoneal treatment cycle, e.g., based on blood pressure and/or other measured patient parameters.

In some embodiments, values relating to system parameter values may be analyzed. Based on the performed analysis, an output may be provided, which may be for example be displayed to a system operator.

It is noted that the system operator can include, for example, a medical professional and/or a patient to be treated by the dialysis system.

In some embodiments, based on the analysis output, system operating parameters may be controlled (e.g., adapted).

Optionally, statistical analysis can be performed using the operating system parameter values, which can be descriptive of Numerical, Categorical, and Ordinal statistical data.

In some embodiments, the dialysis system may have artificial intelligence (e.g., machine-learning functionalities), for example, to automatically generate patient questionnaires, to generate operator questionnaires, to perform UI optimization, to optimize patient treatment, and/or the like.

For example, the dialysis system may automatically control treatment parameter "on-the-go", while the patient is being treated. In some examples, the dialysis system may analyze patient parameters and suggest, based on the performed analysis, a treatment protocol for approval by the operator.

Additional patient parameters that may be taken into consideration include dietary and/or physical exercising behavior and habits, biomechanical parameters, and/or the like.

Furthermore, system operating characteristics may also be monitored to detect system malfunctions such as, for example, catheter blockage, pump malfunction, catheter leakages, and/or the like.

In peritoneal dialysis, which requires surgical insertion of a catheter part into the patient's abdominal cavity and leaving another part of the catheter exposed externally from the patient's body, complications such as infections, catheter blockages and hernia are prominent risk factors.

In many cases, dialysis patient parameters are monitored during the dialysis treatment and dialysis parameters possibly adapted accordingly to modify (e.g., optimize) dialysis treatment, for example, to reduce (e.g., prevent or minimize) the risk of complications and/or to increase treatment efficiency and/or comfort.

Aspects of disclosed embodiments pertains to systems, devices, computer-implemented systems, platforms and/or methods for providing one or more users with information about a plurality of patients including, for example, patients undergoing (e.g., peritoneal) dialysis. The patient information includes physical patient parameter, physiological patient parameter and/or dialysis system parameters for the purpose of determining, based on analysis of the patient information, an output related to a personalized dialysis treatment, for example, to reduce complications, increase treatment efficiency and/or increase patient comfort.

For the at least one patient, respective patient and/or system parameters can be monitored, stored, retrieved and/or analyzed for determining the appropriate dialysis conditions of the specific patient.

According to some embodiments, the physical information can include, for example, patient information such as patient's gender, age, height, race and/or weight; medical examination results and/or diagnosis such as patient's blood, urine and/or feces test results; and/or medical examination results such as anatomic and/or physiologic imaging or diagnosis deduced therefrom, or any other non-invasive or invasive examination results such as endoscopic examination results, and/or the like.

According to some embodiments, there is provided a computer-implemented patient information platform such as, yet not limited to, a website, a computer-implemented application, a computer program or a combination thereof for storing, updating and/or providing patient information associated with specific patients. The computer-implemented platform may be operable to analyze patient information for determining an output related to dialysis treatment for the at least one patient according to the specific patient information.

Patient information may be provided manually and/or automatically to the computer-implemented platform.

In some embodiments, the computer-implemented platform includes an I/O device configured to receive patient input data (e.g., manually from at least one user and/or automatically from one or more sensors monitoring patient and/or system parameters); and an analysis engine configured to analyze the patient input data and to determine, based on the patient input data of the specific patient, output information related to a personalized dialysis treatment. In some embodiments, the patient input data may be updated patient input data.

The patient input data may include for example, general patient data descriptive of, for example, the patient's age, gender, weight and/or height; behavioral patient data descriptive of, for example, dietary and/or physical exercise habits and behavior; and/or physiological patient data descriptive of, for example, medical test and examination results such as blood test results, urine test results, blood pressure and/or pulse values and/or the like.

In some embodiments, the computer-implemented platform (also shortly referred to herein as "platform:") enables several users to input and/or update input patient data and/or to view automatically monitored patient data associated with the same specific patient. Optionally, the patient himself/ herself and professional medical persons treating the patient such as the patient's one or more physicians or medical examination person can input information relating to the same patient's physical condition through the platform e.g. by entering the patient's personal account and inputting information via predefined input fields. Hence, the "user" may, in some embodiments, include the patient in addition or alternative to the medical professional/caretaker.

The patient input data may also include for example, medical history of the patient, previous dialysis and/other treatments given to the patient, medication history and current uptake of the patient and the like.

According to some embodiments, the platform may be configured to collect, for each specific patient, all the patient input data, analyze it to establish a patient medical profile, and determine a dialysis related output information, based on analysis results (e.g. the patient's profile). The output information may include, for example, a dialysis treatment protocol laying out a personalized dialysis adapted for the specific patient, according to the physical and medical condition of the patient deduced by the analysis process.

The dialysis treatment protocol may include, for instance, recommended dialysis parameters such as, yet not limited to, recommended dialysates dosing parameters; timing parameters for the dialysis treatment; dialysis instruments features and/or the like. In some embodiments, the dialysis system may output, based on the performed analysis of the dialysis system parameters, recommendations with respect to adjuvant medications. In some embodiments, based on the performed analysis of the dialysis system parameters, adjuvant medication dosage optimization may be performed to improve treatment outcome.

The dialysates dosing parameters may include for example (for a peritoneal dialysis) the overall fluid volume/ weight, the appropriate type and concentration of each dialysate to be used for the patient, the order of which these dialysates are to be inserted and the like.

The timing parameters may include for example the frequency of dialysis treatments recommended to the patient (once a month, every week etc.), the duration of dialysates fill/drain sessions within each dialysis session (e.g. fluids are to be inserted through the catheter into the abdominal cavity for 10 min, then the patient is rested through a waiting time interval of 20 min and then a drainage is carried out, where this fill and drain process can be repeated several times during a peritoneal dialysis treatment), In some embodiments, the output information may include a prediction about a patient's risk status (e.g., expecting change from "medium risk" to "high risk" in two hours from current time stamp); prioritization for conducting personal visit; providing navigation information for optimized scheduling of patient visits, e.g., according to clinical or medical urgency and/or geographic location of the patient and caretaker; adaptively changing based on the patient input data of the one or more patients, upper and lower limit of fill/drain cycle; adaptively changing display of patient data based on associated level of risk; automatically or manually assigning a risk level to a patient. For example, changing a risk level of a patient may be accomplished by displaying an icon representing a patient and allowing dragging of the icon indicative of a risk level. In some examples, the risk-level icon can or may be dragged from area of the UI associated with a first patient risk level to another UI area which is associated with a second patient risk level that is different from the first patient risk level.

The dialysis instruments features recommended for the specific patient in the dialysis treatment protocol may include for example, the type or features of a catheter recommended, the type and/or features of the fill and drainage containers, and/or fill and drainage recommended pump rate and the like.

According to some embodiments, the platform also enables presenting the output information via one or more presentation and/or output devices such as, yet not limited to, via visual output devices such as a screen, touch screen and/or the like, auditory output devices such as speakers or earphones and/or the like and/or tactile output devices.

In some embodiments, the computer-implemented platform includes a user interface (UI) such as a graphical user interface (GUI). The UI may be configured at least to support updating and inputting of the patient input data and presentation of analysis output for each specific patient and/or a group of patients. A group of patients may be selected based on a selection criterion provided by the user (e.g., the caretaker) and/or automatically by the platform, for example, based on cluster analysis.

Optionally, the UI provides (e.g., graphical) input fields allowing a user to create a patient account that is associated with a specific patient. Patient data may be associated with that account and updated (manually, automatically and/or semi-automatically).

In some embodiments, the UI or part thereof can be a query-based interface for allowing users to input and/or update the patient input data via one or more predefined query structures.

In some embodiments, some patient information may be provided to the platform via predefined input fields and some patient information is designed to be registered via the UI through queries.

In some embodiments, the UI may comprise query input fields for entering user-defined queries for the retrieval of corresponding patient information.

The input fields may allow providing general physical information parameters input fields such as age, gender, weight, height etc., in which the user is required to type the value of the specific parameter into a designated box.

Other input fields may include medical results fields in which the user can upload results of medical examinations and/or diagnosis such as blood test results or text including medical diagnosis and the like.

In some embodiments, a query may be a platform-generated query automatically generated by a query-generation engine. Such platform-generated query may stipulate the user to answer questions of a platform-generated questionnaires, which can be part of the query. The query may be a personalized query. Optionally, the query-generation engine may have artificial intelligence (e.g., machine-learning functionalities) automatically generating, for example, the platform-generated queries (comprising e.g., questionnaires to patients and/or healthcare provider personnel). Optionally, one or more queries may be created by the computer-implemented platform to stipulate the manual updating of patient information including, for example, a behavioral tracking diary of a patient by providing ongoing requests of periodic filling in of input data.

For example, patient input data descriptive of monitored dialysis patient parameters may be analyzed. If the analysis of the monitored dialysis patient parameters yields that an alert-trigger criterion is met, then the computer-implemented platform may generate a personalized query (e.g., patient questionnaire) comprising investigative questions and/or other input fields to be completed by the patient and/or his caretaker to determine why an alert was triggered. For example, an alert indicative of "increased patient weight due to possibly insufficient fluid removal" may result in the display of a questionnaire comprising one or more questions requesting patient regarding fluid intake habits, eating habits, information relating to the patient's digestive system (e.g., information about constipation or lack thereof), and/or the like, to determine whether for example increase in patient weight is due to comparatively inefficient dialysis and/or change in dietary patient behavior and/or digestive disorders (e.g., by employing a microphone and/or any other suitable sensor to monitor the patient's bowl activity). Based on the provided questionnaire input and/or the monitored dialysis treatment parameter values, the computer-implemented platform may provide the user, for example, with personalized dietary recommendations. For example, when fluid removal from the patient's body is measured as being insufficient and the patient-provided feedback indicates excess fluid intake relative to his body weight and height, then platform-generated dietary recommendation may suggest a reduction in fluid intake (e.g., reducing water intake from 12 to 8 cups a day, given an unchanged body activity regime).

The computer-implemented platform may also be configured to automatically identify hazardous patient physical condition and output alerts indicative thereof.

The computer-implemented platform may further be configured to receive monitoring information in real time (RT) or near RT during a dialysis treatment session indicative of patient's condition during the dialysis treatment, analyze the received monitoring information and, when required, modify the dialysis treatment and/or output information indicative of the analysis results.

For example, the platform may analyze the monitoring information received from one or more external monitoring devices, which monitor physical parameters of the patient during the dialysis in RT or near RT such as the patient's blood pressure (e.g., systolic, diastolic, mean arterial pressure), pulse rate, breathing rate, breathing pattern, oxygen saturation level, heart rate, bodily fluid (e.g., blood, sweat, tears and/or saliva) analyte concentration (e.g., hemoglobin, cholesterol, glucose, toxins, hormone level, magnesium, calcium; salts; etc.); weight, body-mass index (BMI); pH level; electrical property of the patient's skin (e.g., conductivity, resistance); patient motoric function; electrocardiogram, myocardiogram, electroencephalography (EEG), capnography values, and/or cognitive ability of the patient; an (e.g., sound) sensor for measuring bowel activity; and/or an electromyograph sensor for detecting a muscle spasm of the patient.

The patient parameters are processed to determine whether the treatment being currently given to the patient should be modified, e.g., to improve treatment and/or to prevent complications and/or to improve the patient's subjectively perceived level of wellness. If a modification is required, the platform may output an alert; output the dialysis parameters that should be modified and the manner in which they should be modified; and/or automatically modify the dialysis treatment by being operationally associated with the dialysis device.

In some embodiments, the computer-implemented platform may be operable to predict, based on patient data received at the platform during a recent monitored time interval, the onset of complications related to peritoneal patient treatment and predict an estimated future time stamp or future time interval of the onset of such complications.

Reference is now made to FIG. 1, which is a block diagram schematically showing a computer-implemented platform (CIP) 1000, for providing users with patient information, according to some embodiments. CIP 1000 may be implemented as part of a dialysis system 50, as schematically shown in FIG. 1.

CIP 1000 may be implemented by a computerized device including, for example, a multifunction mobile communication device such as a "smartphone", a personal computer, a laptop computer, a tablet computer, a server (which may relate to one or more servers or storage systems and/or services associated with a business or corporate entity, including for example, a file hosting service, cloud storage service, online file storage provider, peer-to-peer file storage or hosting service and/or a cyberlocker), personal digital assistant, a workstation, a wearable device, a handheld computer, a notebook computer, a vehicular device, a stationary device and/or a home appliances control system.

In some embodiments, the CIP 1000 may include an Input/Output (I/O) device 1100 comprising, for example, a user interface 1102; an analysis engine 1300; a display device 1400; a communication device 1500; and a dialysis monitoring and control engine 1600.

According to some embodiments, the I/O device 1100 may be configured to receive initial input data, for each dialysis treatment patient, the patient input data including patient-related information associated with the specific patient. The patient input data may be received via the UI 1102 allowing inputting patient input data via predefined input fields, one or more questionnaires, and/or one or more query-based diaries and/or may be retrievable from one or more other data sources.

According to some embodiments, the analysis engine 1300 may be configured to receive the initial input data of the respective patient and to receive in RT or near RT monitoring data, indicative of physical condition of the respective patient and/or of the dialysis device 11 being used, during dialysis treatment of the respective patient, analyze the received patient initial and monitoring data (e.g. in RT or near RT in respect to the treatment time), to determine, based on the received patient initial and monitoring data, output information related to the patient in respect to the dialysis treatment he/she undergoes.

According to some embodiments, the analysis of the initial input data of the respective patient, may be done to determine an initial risk level of the patient (e.g. by associating of the patient to an initial risk profile group such as high risk, low risk or no-risk level), e.g. by determining the patient's physical condition at a time that is in proximity to the dialysis treatment session time and associating the determined physical condition of the patient to one of the risk profile groups, using one or more analysis programs, algorithms, processing devices and/or methodologies. The initial input data may include for example, medical and/or behavioral history of the patient (e.g. including latest and/or accumulated physical, psychological and/or medical tests results and/or diagnosis, patient's responsiveness to previous dialysis treatments, patient's daily life style related habits, etc.), gender, age, weight and/or height of the patient, etc.

According to some embodiments, once the dialysis treatment of the respective patient begins, the analysis engine 1300 and the dialysis monitoring and control engine 1600 may collect, in RT or near RT, monitoring data directly or indirectly indicative and/or influencing the patient's physical condition when undergoing the dialysis treatment. The monitoring data may include for example, information indicative of the operational functioning of the dialysis device 11, the dialysis system 50 and/or measured physical characteristics of the patient such as body temperature, blood pressure, pulse, oxygen saturation etc. The analysis engine 1300 may be configured to use both the initial input data and the monitoring data of the patient, to identify in RT or near RT, in respect to the dialysis treatment session timing, one or more anomalous physical characteristics of the respective patient, determine whether one or more of the identified anomalous physical characteristics are related to the dialysis treatment session, and to determine an (e.g., updated) risk level of the respective patient and optionally, based on the anomalous physical characteristics identification.

Some anomalous physical characteristics may not be associated to the dialysis treatment session, in cases, for example, where the patient has a known background ill condition that cannot affect the patient's response to the dialysis treatment or that although puts the patient under some risk to develop dialysis treatment complications, will not exclude the patient for going through this life saving process. For example, a patient having a preconditioned sever overweight or severe underweight, old age, etc. may be considered high risk patient as the patient's initial risk level, but may still be required to undergo the dialysis treatment due to the patient's more threatening kidney functioning severity. In this example, the updated risk level of the patient may remain the same as his/her initial high risk level, even when updated anomalous physical characteristics are identified during the dialysis treatment of the patient. In this case, when one or more of the anomalous physical characteristics of the respective patient are related to the treatment itself, the CIP 1000 may automatically display output information to the professional user(s) via the display device 1400, to enable the professional staff to address these "dialysis treatment related anomalies" as quickly as possible.

According to some embodiments, the display device 1400 may be configured to show the updated risk level of each monitored patient and to distinctively display patients undergoing dialysis treatment that are showing anomalous physical characteristics that are related to their dialysis treatment.

In some embodiments, the dialysis system may be configured to automatically differentiate or distinguish between dialysis-related and non-dialysis related anomalous physical characteristics.

In some embodiments, the dialysis system may be configured to provide an output to indicate (e.g., a user) which anomalous parameter value is dialysis-related and which not.

In some embodiments, the output may include annotations, labels, colors, and/or other objects and/or display modes for providing information about dialysis-related and non-dialysis related anomalous physical characteristics.

In some examples, the output may pertain to objects (e.g., labels, annotations, symbols, widgets, text) and/or different display modes (e.g., blinking, non-blinking, different colors), presented in association with information pertaining to (e.g., descriptive of) the dialysis-related and/or non-dialysis related anomalous physical characteristics.

For example, the patient's initial input data may also include values and/or status indications of one of more patient parameters indicative of the patient's condition such as identified anomalous physical characteristics derived from the patient's initial input data such as over/under weight of the patient, and/or dialysis treatment related information such as identified anomalous physical characteristics related to the dialysis treatment session. The analysis of the patient input data may be performed to determine a personalized patient dialysis protocol output information. The dialysis protocol of the patient may include for example, dialysis parameters setting a dialysis program for the specific patient.

The dialysis parameters recommended for the patient's treatment may include, for example, dialysates dosing, dialysate types, dialysis instruments parameters, instrument types, sensor types, dialysis recommended treatment frequency, treatment timing parameters, etc.

According to some embodiments, the display device 1400 may be configured to display the output information of the analysis engine 1300 and optionally also for supporting presentation of the UI 1102.

All input and output data of the CIP 1000 may be stored via one or more storage units such as databases along with patients' identification information. For example, at least one of a plurality of patients (e.g., each patient) may be associated in the database with a patient account having patient' personal data such as name identification (ID) number, account serial number and the like, associated with one another and with the input and output data associated with this patient.

The UI 1102 may provide users with access to patient's personal accounts via a security mechanism that requires, for example, entering one or more identification and/or security codes.

According to some embodiments, the communication device 1500 may be configured to transmit and receive data from one or more external systems such as for communication with the dialysis device 11, an external monitoring system (e.g. including one or more patient monitoring devices), configured to monitor the patient's treatment, one or more remotely located operators and/or the like.

According to some embodiments, the dialysis monitoring and control engine 1600 may be configured for RT or near RT monitoring of the patients during a dialysis treatment session, resulting in monitoring information; for RT or near RT analysis of the monitoring information; and optionally also for RT or near RT control of the dialysis session (e.g. by controlling the dialysis device 11 operation), based on analysis results.

The monitoring may be done, for example, by receiving RT or near RT monitoring data from one or more monitoring devices such as one or more sensors. The sensors may be attached to the patient during the dialysis treatment session or be configured to measure physical condition related parameters of the patient from a distance. The attached sensors may include, for instance, a thermometer for temperature measurements, a blood pressure device, a pulse meter, a saturation measuring sensor or device and/or the like.

In some embodiments, the dialysis monitoring and control engine 1600 may be configured to enable users such as caretakers monitoring the patient during treatment, to input monitoring information e.g. via one or more designated UI 1102 tools.

According to some embodiments, the dialysis monitoring and control engine 1600 may also be configured to operate the monitoring devices and directly and/or indirectly receive monitoring information therefrom.

In some embodiments, analysis of the monitoring information may yield an output indicative of a hazardous patient condition, the CIP in these cases, may output alerts via the UI 1102 and/or any other alerting device for indicating the hazardous situation.

In some embodiments, the dialysis monitoring and control engine 1600 may also be configured for automatic treatment modification, for example by being operatively associated with one or more of the dialysis devices for modifying the patient's treatment in RT during thereof.

Figure 2:
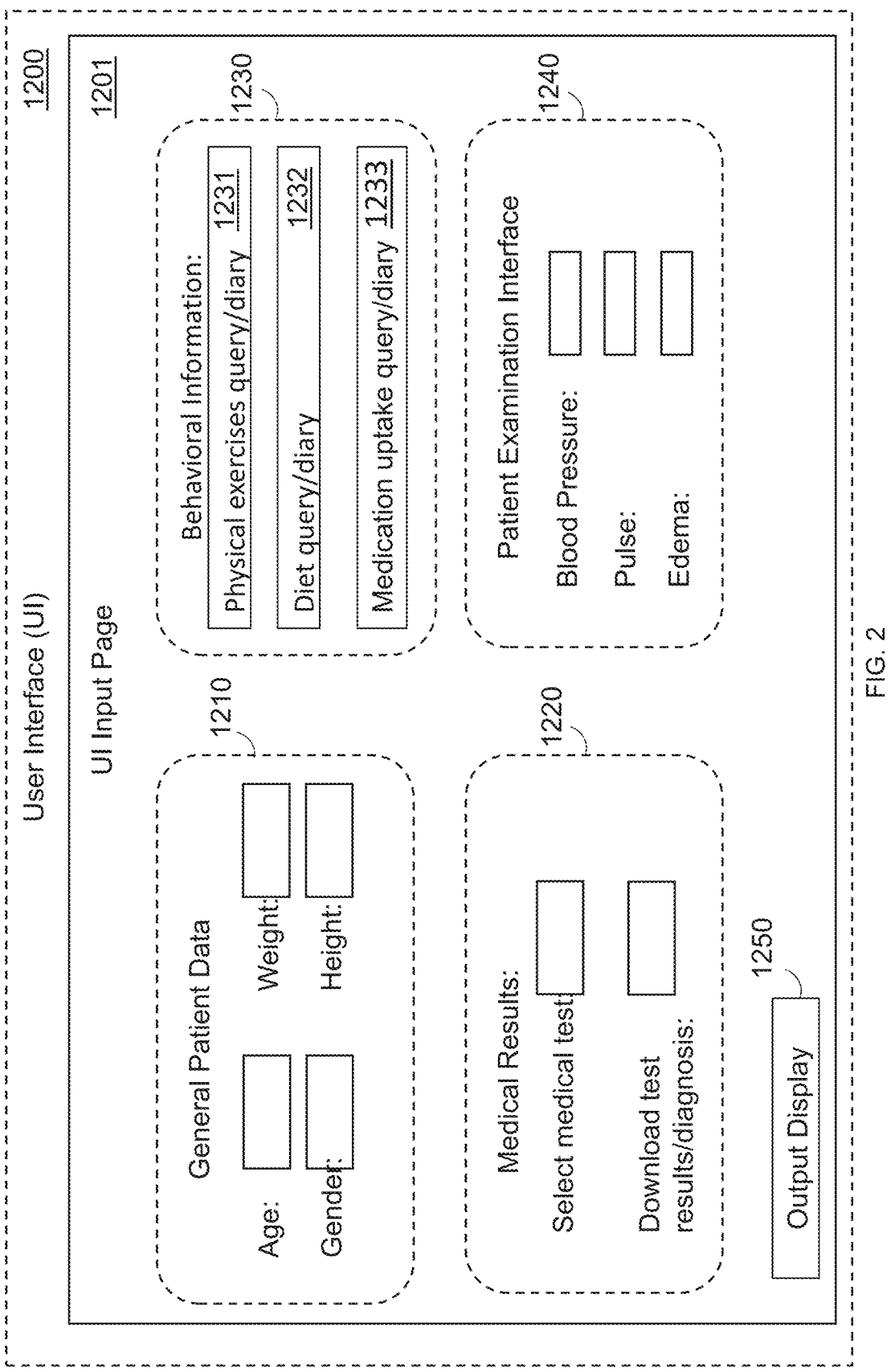
FIG. 2 is a block diagram, schematically illustrating a user interface of the computer-implemented platform, according to some embodiments.

FIG. 2 shows a block diagram, schematically illustrating one optional input page 1201 of the UI 1102, which is a platform for enabling users to input patients' initial input data therethrough, according to some embodiments of the UI 1102.

The UI input page 1201 may be divided into several input fields groups and several diary or questionnaire input options.

For example, a first group of input fields may be designated to receive physical patient parameters 1210 including, for example, the user to input the patient's age, gender, weight, height etc., e.g., by simply typing the value into a designated field box.

For example, a second group input fields may be designated to receive values relating to physiological patient parameters 1220 including, for example, medical results, written diagnoses and/or treatment recommendations for a respective patient.

A UI component 1230 for enabling inputting and/or updating patient behavioral parameters may include, for example, a physical exercise questionnaire, and/or a diary tool 1231 is designed for enabling the patient to input behavioral information relating to physical exercising habits and abilities.

A diet questionnaire and/or a diary tool 1232 may be designed for enabling the patient to input behavioral information relating to his dietary habits, physical exercising routine, medication uptake routine, etc.

A medication uptake questionnaire or a diary tool 1233 is designed for enabling the patient (as a user in this case) to input behavioral information relating to his medication consumption habits and optionally also for indicating substances that the patient is negatively responsive to such as substances to which the patient is allergic.

The UI 1102 may also provide a patient examination interface 1240 for enabling users such as the patient himself/herself, to input currently checked parameters such as, for example, blood pressure, pulse rate, body temperature, edema condition etc. For example, the computer-implemented platform may comprise a camera operable to determine characteristics of indentations in tissue because of pressure applied to the patient's tissue for determining edema or lack thereof. Identification of an edema may a clinical condition providing an indication that an anomalous parameter value of a physical characteristic such as patient overweight is due to insufficient ultrafiltration, rather than due to excess food intake, which is an example of a non-dialysis related anomalous physical characteristic. Additional or alternative measures and/or clinical conditions may provide indications concerning dialysis and non-dialysis related (anomalous parameter values) of a physical characteristic.

The patient can self-examine him/herself by using available measuring devices or via a guided self-examination process to input current RT checked physical parameters.

For example, the patient or a caretaker thereof can input those self-examined parameters values right before a dialysis treatment session. This RT parameters can be further considered in the analysis of all the patient input data.

According to other aspects of the disclosed embodiments, there is provided a method for providing at least one user with patients' specific physical information. The method includes at least receiving patient input data from at least one user, the patient input data including at least patient related physical information; analyzing the patient input data to determine, based on the patient input data of the specific patient; and outputting information related to a personalized dialysis treatment, based at least on the analysis of the patient input data. In some embodiments, different types and/or forms of patient input data may be given corresponding (e.g., different) weight. In some embodiments, various modalities may be employed to generate the patient input data. For example, patient input data may be based on sensor measurements and/or on user-provided input.

In some embodiments, UI input page 1201 may be configured to invoke a dialysis system treatment calibration procedure. For example, based on the analysis of the patient input data, dialysis control engine 1600 may automatically initiate a dialysis system calibration procedure. In another example, dialysis control engine 1600 may request the user to initiate dialysis system calibration steps or approve execution of a suggested dialysis system calibration protocol.

In some embodiments, self-calibration of treatment parameter values pertaining to the operation of dialysis device 11 may be invoked manually or automatically. Self-calibration may for example be performed as disclosed in International Patent Application WO2018/142406 filed on 1 Jan. 2018, titled "Smart Peritoneal Dialysis Device", and which is incorporated herein by reference in its entirety.

For example, measured light absorption and/or scattering values and/or indication of the drained dialysate and the fresh dialysate may be compared with each other. Comparing drained dialysate measured parameter values to fresh dialysate measured parameter values, allows for example self-calibration of treatment parameter values, for example to reduce or minimize treatment variations due to different batches of fresh dialysate.

In some examples, the measured light absorption and/or scattering values and/or values indications of the drained dialysate are compared to stored indications and/or to a table in a memory of the dialysis system. Optionally, the measured values and/or values indications of the drained dialysate are compared to stored values and/or values indications of a previously drained (also: used) dialysate.

As mentioned above, the patient initial input data may also include general patient data such as the patient's gender, age, weight etc.; patient behavioral data such as physical exercising and/or dietary behavior; and/or patient medical test and examination results.

The at least one output determined by the analysis engine may include one or more personalized dialysis parameters associated with the specific patient such as, for example, a dialysis treatment protocol, dialysis treatment timing parameters; dialysates parameters and/or the like. Information relating to the output may be displayed via an output display 1250.

The output information, resulting from the analysis of the patient input data, may be presented via one or more output devices.

The query-based platform of the UI may include one or more of: general physical data of the patient; medical results and/or diagnosis of the patient; behavioral information relating to the patient; patient current examination results.

The method may further include monitoring the patient during the dialysis treatment by receiving monitoring information and analyzing thereof in RT or near RT.

For example, the analysis of the monitoring information may identify a hazardous patient condition, in which case, one or more alerts may be outputted or transmitted via the UI or any other alerting device for indicating the hazardous situation.

The method may further include controlling the dialysis treatment by enabling modification of one or more of the dialysis parameters.

For example, in case of a peritoneal dialysis, the dialysis parameters may include dialysates types and dosing; fill/drain rate control parameters such as pump power; treatment related timing parameters and the like.

The monitoring may be done by receiving RT or near RT monitoring data from one or more monitoring devices such as sensors; and the controlling or modification of the dialysis treatment may be done by automatically modifying dialysis operations, or by outputting in RT or near RT dialysis treatment parameters, deduced based on the analysis carried out to the monitoring information, for manual modification of the dialysis treatment.

The automatic modification of the treatment parameters may be carried out by transmitting operational commands to the dialysis device.

The CIP 1000 may communicate with the dialysis device 11 via a communication link 21 for retrieval of operational information therefrom and/or for enabling modification of functions thereof.

The term "communication link" used herein refers to any communication technology and method, such as, yet not limited to, wireless and/or wired communication, using any one or more known communication protocols and formats including, for example, Wide Area Network (WAN), Local Area Network (LAN) employing, e.g., Wireless Local Area Network (WLAN)), Metropolitan Area Network (MAN), Personal Area Network (PAN), extranet, 2G, 3G, 3.5G, 4G including for example Mobile WIMAX or Long Term Evolution (LTE) advanced, Bluetooth® (e.g., Bluetooth smart), ZigBee™, near-field communication (NFC) and/or any other current or future communication network, standard, and/or system.

The dialysis device 11 may be associated with a treatment monitoring system 12, which may be external to the CIP 1000 or part thereof. The communication device 1500 may retrieve input monitoring information from the treatment monitoring system 12.

The treatment monitoring system 12 may be configured for monitoring physical condition of the patient being treated and/or dialysis equipment conditions.

The communication device 1500 may also enable communication with a remote operator 13 via a communication link 22, for allowing remotely located users, to view treatment related information in RT, near RT or offline.

The remote operator 13 may use the CIP 1000 UI in long distance as an end user to also monitor the dialysis treatment in RT and optionally also communicate with the dialysis device in RT or near RT via a communication link 23, e.g. for also controlling the dialysis device 11.

Dialysis device 11 and/or treatment monitoring system 12 may be considered being part of dialysis system 50.

The communication device 1500 may be configured for communicating with one or more systems or devices that are external to the CIP 1000, via one or more communication links 21-23.

The CIP 1000 may further include a memory 1702 and a processor 1704, which may be configured, for processing, storage and/or retrieval of data related to system parameters including, for example, patients' personal identification information, patients' input data, patients' output data, monitoring data and/or the like. Data stored in memory 1702 may be structured such that the at least one patient of a plurality of patients (e.g., each patient) known in the CIP 1000 is associated with information relating thereto.

Figure 3B:
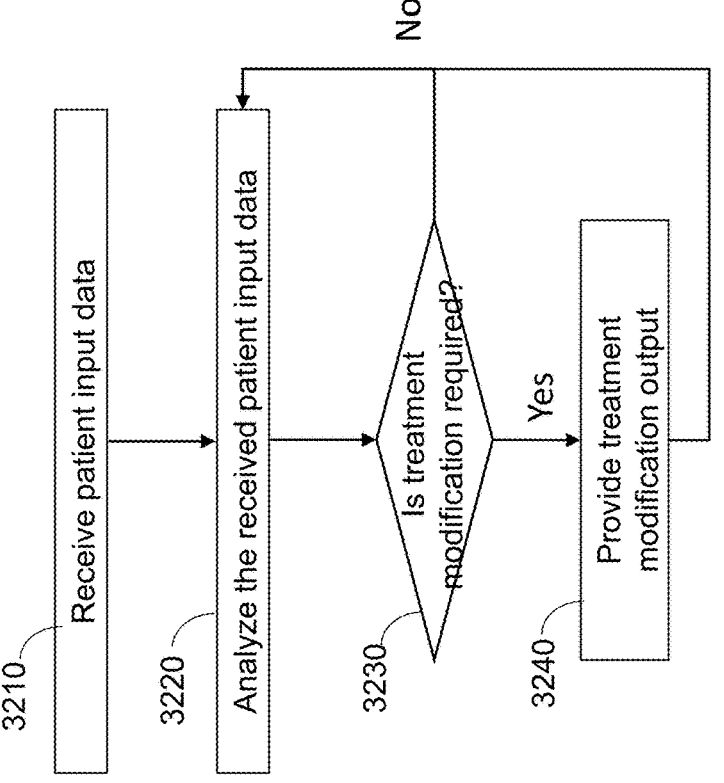
FIG. 3B is a flowchart of a method for schematically illustrating a process for real time monitoring of a patient during dialysis treatment thereof, according to some embodiments.
Figure 3A:
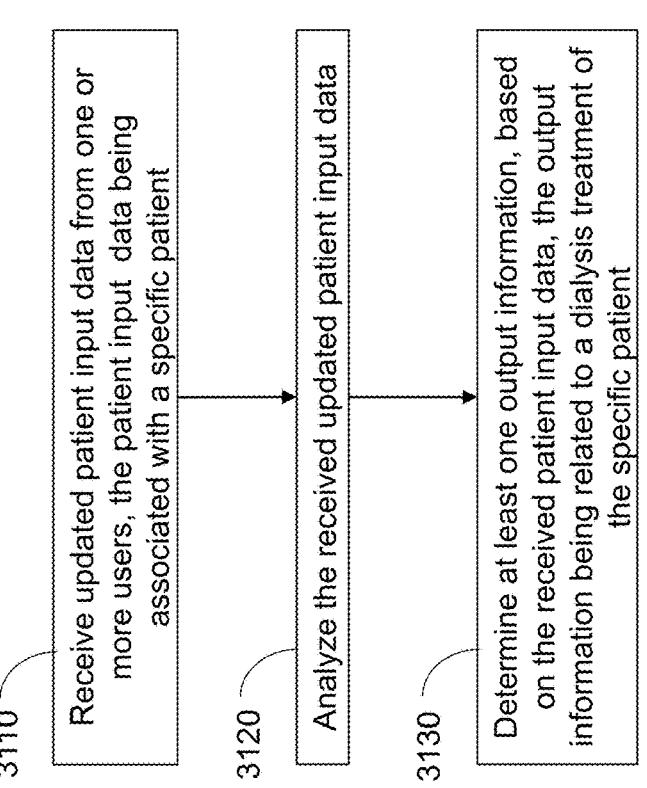
FIG. 3A is a flowchart of a method for providing at least one user with patient-related physical and/or physiological information, according to some embodiments.

Reference is now made to FIG. 3A, schematically illustrating a method of providing at least one user with patient information of one or more patients, according to some embodiments.

As indicated by block 3110, the method may include receiving patient input data relating to one or more patients.

As indicated by block 3120, the method may further include analyzing the received patient input data.

As indicated by block 3130, the method may further include determining, based on the received patient input data, at least one output relating to a dialysis treatment of the respective one or more patients. The output may comprise, for example, a personalized dialysis treatment protocol including, for example, treatment parameters values and/or statuses indicative of various dialysis treatment aspects tailored for the specific patient, according to his/her personal patient input data. The resulting output information can be presented via one or more presentation devices such as via visual and/or auditory display.

FIG. 3B shows a process for monitoring and controlling of a patient during dialysis treatment thereof, according to some embodiments.

As indicated by block 3210, the monitoring and controlling process includes ongoing and RT or near RT receiving of input monitoring information indicative of the patient's condition during a dialysis treatment and/or of the dialysis device related parameters.

As indicated by block 3220, the method may further include analyzing of the received patient input data.

The patient input data may be received from one or more monitoring devices and/or systems. The monitoring system and/or device may include one or more sensors for measuring patient parameters before, during and/or after the dialysis treatment such as, for example, body temperature, blood pressure, pulse, saturation and/or the like, for determining the patient's response to the treatment and during the treatment as well as the dialysis operational parameters such as fill/drain rate, catheter flow rate and the like.

As indicated by block 3230, the analysis can include determining whether treatment modification is required. If the performed analysis yields that a treatment modification criterion is met, then a corresponding treatment modification output may be provided (block 3240). The treatment modification criterion may pertain to, for example, patient parameter threshold values.

The treatment modification output may for example be indicative of a selected patient treatment being potentially harmful; comprise output modification information presented to a user and/or comprise an output command for automatically adapting of a patient treatment, for example, by providing a corresponding control output to a dialysis pump, a dialysate heater, and/or the like.

The treatment modification output may also pertain to dialysis system operating parameters including, for example, system malfunction information (e.g., blocked catheter), insufficient fill/drain flow rate, and/or the like.

According to some embodiments, there is provided a system for providing at least one user with patients' specific physical information. The system may comprise the patient information platform.

The system may include a controller configured to receive patient input data from at least one user, the patient input data comprising patient related physical information, analyze the patient input data to determine, based on the received patient input data of the specific patient, and output information relating to a personalized dialysis treatment.

In some embodiments, the controller may be implemented by a processor and a memory. The memory may store instructions which, when executed by the processor, results, methods and/or processes exemplified herein.

The system enables users such as patients and professional persons such as physicians to input and view medical related information of a patient and output information relating to, for example, recommended dialysis treatment characteristics that are adapted to the specific patient and his/her specific medical/physical condition and history.

The output monitoring information may include instructions for how the dialysis treatment should be modified and/or input monitoring information parameters that should be addressed by the caretakers.

The dialysis treatment referred to above can be any dialysis treatment such as, yet not limited to, peritoneal dialysis, hemodialysis, hemofiltration, hemodiafiltration and intestinal dialysis.

According to some embodiments, the analysis engine may be further configured to analyze initial and monitoring data of multiple patients undergoing a dialysis treatment, to generate updated statistical information indicative of one or more of: the number of patients associated with each risk profile group; the number of patients for whom one or more anomalous physical characteristics have been identified; the number of patients for whom one or more anomalous physical characteristics relating to their dialysis treatment have been identified; wherein the updated statistical information can be displayed by the display device via a combined monitoring display.

Figure 4:
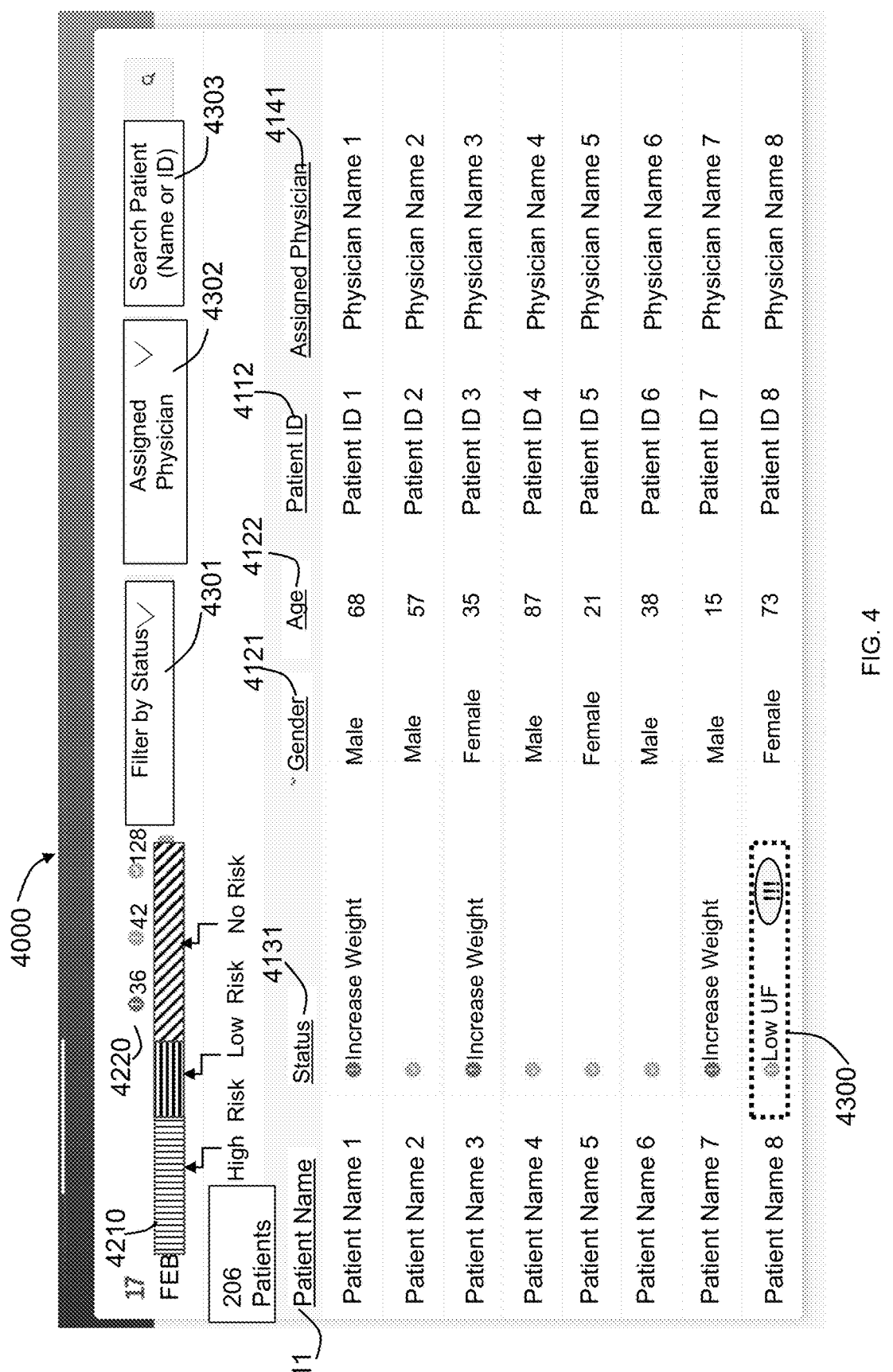
FIG. 4 is an example screenshot of the user interface showing for a combined monitoring display, for displaying information of a plurality of patients undergoing dialysis treatments, according to some embodiments. Optionally, the user interface enables the user to cause the selective display of patient data according to one or more patient display criteria.

FIG. 4 is an example screenshot of the UI showing a combined monitoring display 4000 of a plurality of patients, according to some embodiments.

According to some embodiments, the combined monitoring display may include:

visual display of a table/list displaying information of all patients undergoing dialysis treatment, displaying, for the at least one patient of a plurality of patients undergoing treatment (e.g., each patient), patient information indicative of at least one of: patient identification information (4111, 4112), professional staff member associated with the respective patient (4141), patient initial input data or part thereof (4121, 4122), patient initial and/or updated risk level, patient status 4131, indicative, for example of one or more identified anomalous physical characteristics, patient one or more identified anomalous physical characteristics that are related to the patient's dialysis treatment 4300; and updated statistical information indicative of statistics of all patients undergoing dialysis treatment such as a chart (e.g. pie or bar chart) 4210 indicative of updated statistics of number of patients in each risk profile group, and/or the actual number of patients in each profile group 4220.

The combined monitoring display 4000 may further be configured to enable visual distinction of patients identified with one or more anomalous physical characteristics that are related to their dialysis treatment such as shown in 4300.

According to some embodiments, the UI combined monitoring display 400 may be modulated by the user(s), e.g. by using one or more display filters, allowing the user(s) to adjust the display, according to their selected filtering.

For example, the user(s) may select one of multiple status filtering options, using a status filtering input field 4301, one of multiple assigned physician filtering options, using the assigned physician filtering input field 4302, and/or one of multiple patients filtering options, using the patients filtering input field 4303. The display of the combined monitoring display may be modified according to user(s) selection. For example, the user may select sorting of the patients according to their updated risk level showing patients of higher risk level or higher risk profile group at the top of the list/table and patients of lower updated risk levels at the bottom of the list/table. In another case, the patients may be sorted based on anomalous physical characteristics that are associated with their dialysis treatment.

According to some embodiments, a special designated alert may be issued by the CIP 1000 once hazardous anomalies are identified. The alerts may be distinctively displayed over the display device 1400 (e.g. as popup alerts indicating the anomalies and the patient's details) and/or directly transmitted to the assigned physician's mobile device. The alerts may be displayed via any one or more devices of the display device 1400 such as auditory alerts outputted via audio device(s), visual alerts outputted via visual display devices (e.g. screen) and the like.

In the example screenshot shown in FIG. 4, a clinical status is displayed for at least one of the plurality of patients (e.g., each patient) such as "high risk", "low risk", and "no risk". For example, a "high risk" status may be associated with "increased (patient) weight", "high sugar", "high blood pressure", and/or the like. A "low risk" status may be associated with a low ultrafiltration value ("low UF") 4300.

In some embodiments, one or more filters may be selected by adjusting, for example, sliding bars boundaries displayed to the operator of the UI. In one example, by clicking on or otherwise actionably engaging a corresponding of the displayed chart (e.g., bar section), only the information associated with the respective chart section may be displayed. For example, responsive to clicking on the "high-risk" bar section, only information of high risk patients may be displayed.

In some embodiments, different groups of patients may be associated with different patient parameters such as risk categories. For example, an increase in patient weight by 2 kg within 2 weeks into treatment may be categorized under "high risk" for a first group of patients, whereas an increase in weight by 2 kg in over 2 weeks into treatment may be categorized under "low risk" for a second group of patients. A plurality of patients may be associated with different groups, for example, in accordance with the patients' association to Health Maintenance Operators (HMOs), and/or other dialysis system operating parameters.

In some embodiments, a medical professional may manually associate different patient parameters to different risk categories using designated UI tools. For example, a first physician may associate a low UF value to a "low risk" status, whereas a second physician may associate a low UF value to a "high risk" status. In some embodiments, at least certain "high risk" associated patient parameters (e.g., "increased weight") may be non-configurable by the medical professional.

Figure 5C:
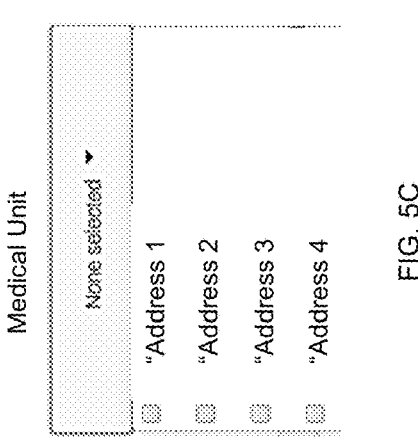
FIGS. 5A-C, FIG. 6 and FIGS. 7A-B show example user interfaces for selecting system parameters, according to some embodiments.
Figure 5B:
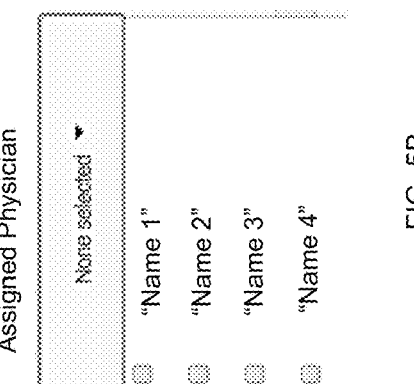
Figure 5A:
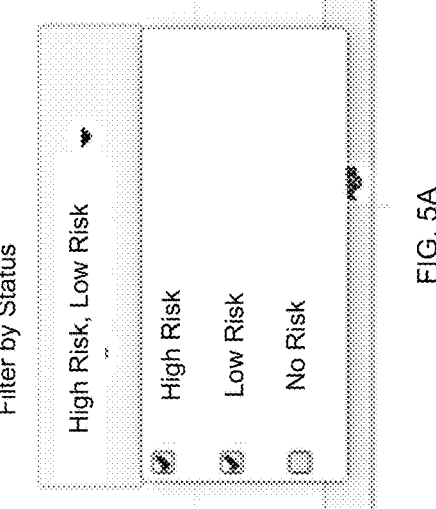

Additional information that may be displayed with respect to the at least one patient (e.g., each patient) may include, for instance, the patient's gender, age, patient ID, and the name of the assigned physician. Additional information can include the respective treatment protocol or regime. A manager or operator of such platform for implementing a Digital Dialysis Center may thus view for the at least one patient (e.g., each patient) the respective treatment protocol or regime. Corresponding information display filter configurations may be selected. As shown in FIG. 5A, one or more risk statuses, a physician may be selected; as shown in FIG. 5B, one or more physicians may be selected; and, as shown in FIG. 5C, one or more medical centers may be selected.

In some embodiments, the dialysis system may perform a physician-based analysis of the various treatments and clinical outcomes. For example, although the same treatment regime may be applied by different physicians, the clinical outcomes may differ, even for patients with apparently non-significant differing patient parameters. As a result of measuring unexpected deviating clinical outcomes, the dialysis system may display questions as an investigative tool to determine the reasons for the deviating clinical outcomes. Optionally, these questions may be generated, for example, using an engine which is based on artificial intelligence.

In some embodiments, the dialysis system may also serve as a platform for performing clinical trials and, for example, supervise the physicians conducting the clinical trials, monitor patient adherence and/or serve as a platform for gathering and, optionally, analyzing the various results of the trials.

Figure 6:
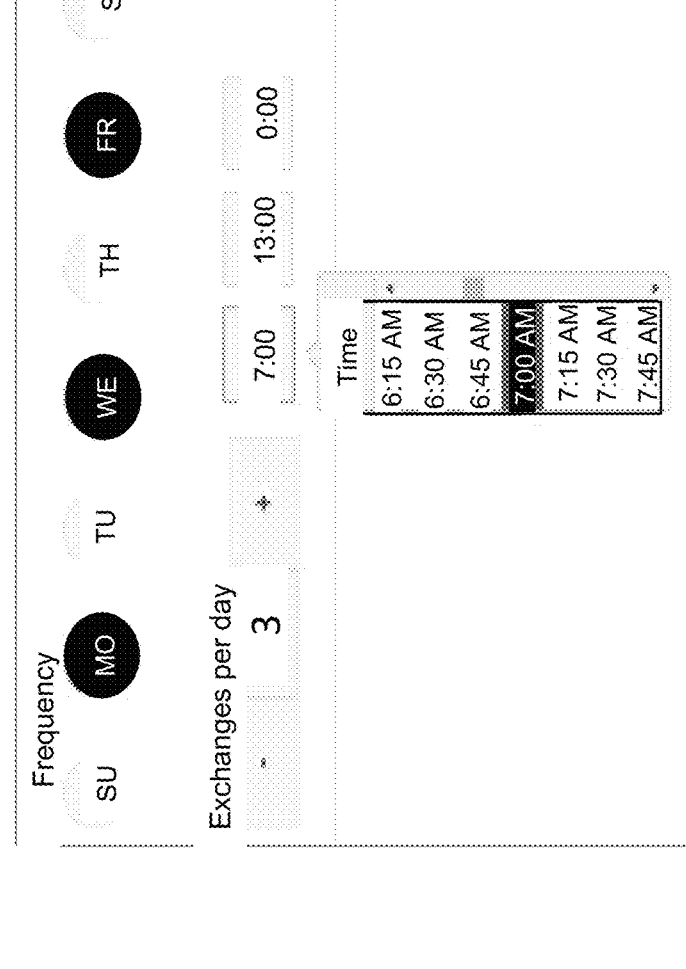
Figure 6:
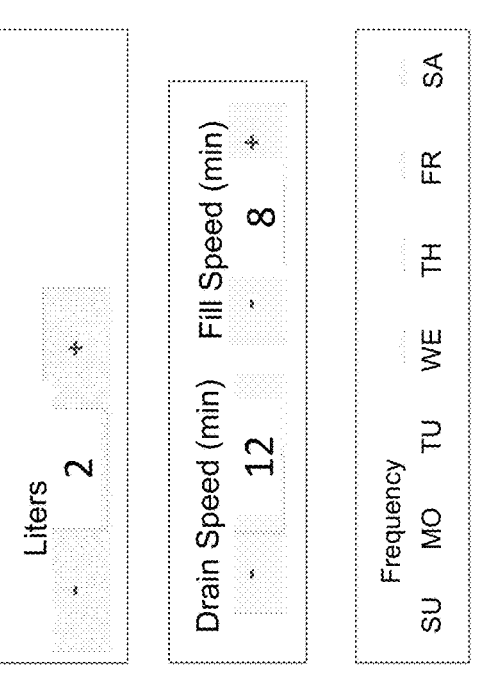
Figure 6:
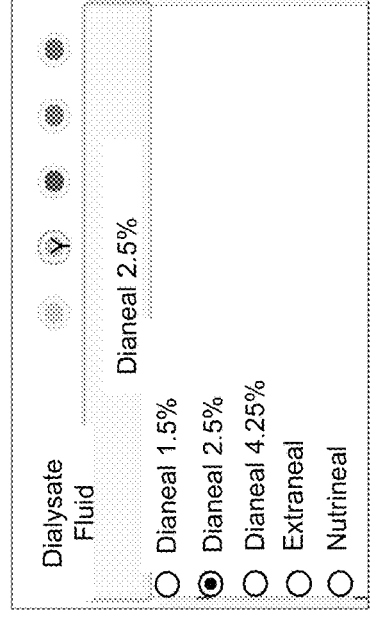

Referring now to FIG. 6, the user interface 1102 allows a medical professional to select, the at least one patient (e.g., each patient), a variety of treatment parameters. For instance, the volume of dialysate fluid, fill speed, drain speed, the number of exchanges per day, etc., may be selected by actionably engaging "+" and "−" symbols. Optionally, an added exchange may be deleted. The scheduled times of a dialysis cycle may be also be selected (e.g., day of week by selecting the corresponding "day" symbols which may then become differently colored, e.g., with filled background color, fresh dialysate fill start time and/or used dialysate drain start time may be selected, for example, via a drop-down list). The number of exchanges (treatment cycles) may also be selectable via user interface 1102. Moreover, the type of osmotic agent and corresponding agent concentration may also be selectable, for example, via radio or option buttons. Different types of dialysate fluids may be associated with different color codes. A matching color code may be printed on or otherwise coupled with the dialysate fluid bag used by the patient.

In some embodiments, default values may be provided. Default values may pertain to, for example, default fill time, default minimum fill time, default maximum fill time; default dialysate fill temperature, minimum default fill dialysate temperature, maximum default fill temperature; minimum blood pressure, maximum blood pressure; default drain time, minimum default drain time limit, maximum default drain time; low UF formula values based on a volume difference between the previous fill and the drained volume in the current exchange, e.g., expressed in percentages; an utilization status (number of dialysis devices out of total available devices currently being used or which were used during a certain time period); and/or a value relating to patient adherence, e.g., number of treatment skips with respect to a prescribed treatment regime.

Figure 7B:
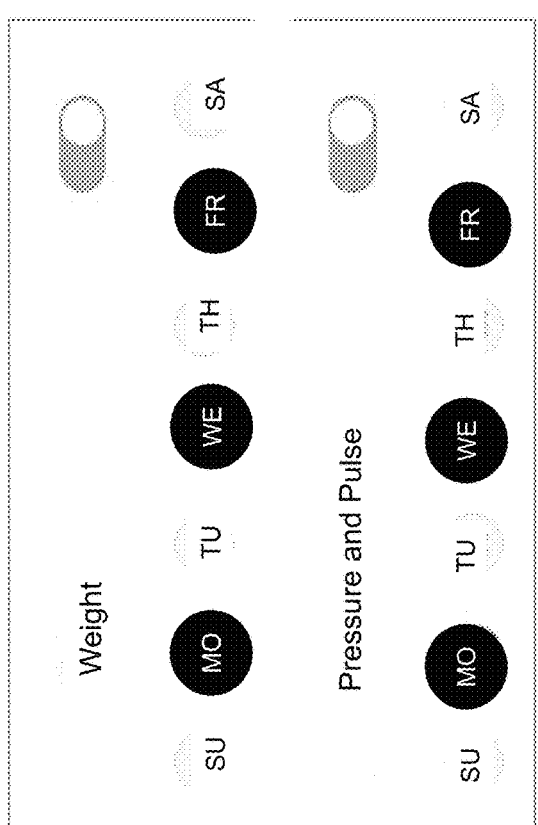
Figure 7A:
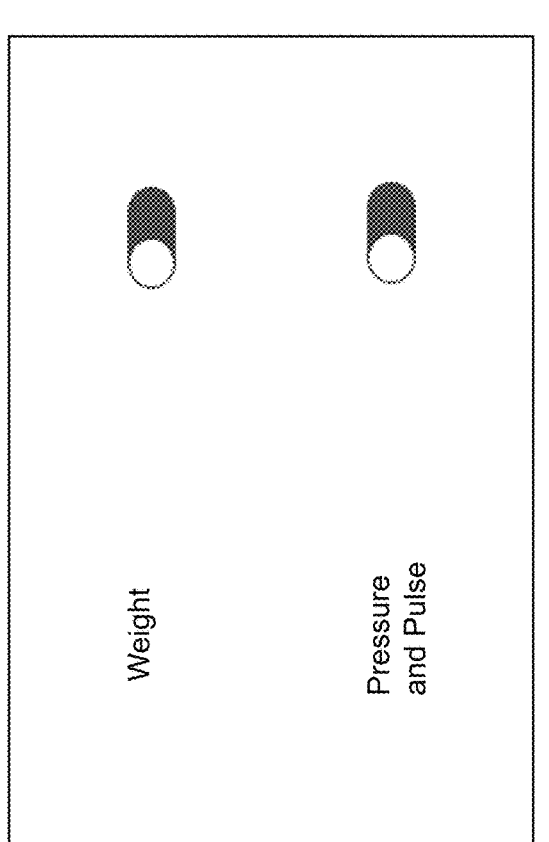

Additional reference is made to FIGS. 7A and 7B. According to some embodiments, an operator may select whether a patient shall be subjected to certain follow-up checks prior and/or after performing a dialysate cycle. For instance, when an operator selects that a patient's weight, pressure and/or pressure is to be measured, the days on which the measurements must be taken are revealed. FIG. 7A exemplifies an interface without selecting that weight, pressure and pulse measurements should be performed, and FIG. 7B exemplifies an interface in which the days are revealed, according the patient's treatment plan, on which the patient is required to have, for instance, weight, pressure, pulse and/or other patient parameter measurements be taken.

Figure 8:
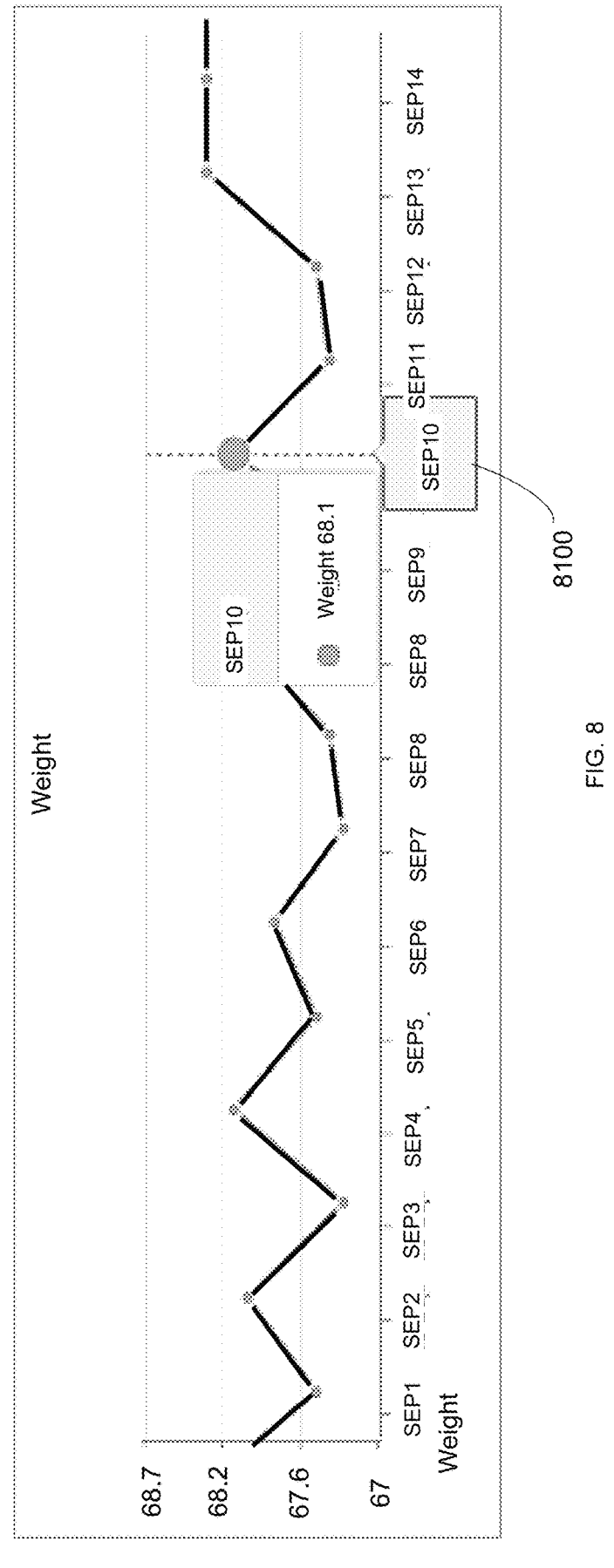
FIG. 8 shows an example graph of a measured patient parameter value.

Further referring to FIG. 8, graphs or plots may be presented to the operator pertaining to a system parameter including, for example, a patient parameter. For example, a patient's weight measurement values, as measured on the respective dates, may be displayed. Optionally, a slider symbol 8100 may be provided allowing the operator to select a specific date for display of the respective patient parameter value. Optionally, the interface may allow the operator to zoom in and zoom out of date ranges.

In some embodiments, the platform may be configured to adaptively change a characteristic of a plot (e.g., color and/or dash type may) depending on whether the displayed values are within an allowed range or not. For example, portions of graph within an allowed range may be displayed in green, and portions of a graph exceeding an upper threshold of the allowed range may be displayed in red, and portions of a graph dropping below a lower threshold may be displayed in yellow. In some examples, the upper and lower thresholds of a range may be displayed together with the plot.

Optionally, for the same or for a plurality of patients, trends and/or gradients relating to system (e.g., patient) parameter values may be displayed. Optionally, upper and/or lower values relating to system (e.g., patient) parameter values may be determined, operator-selected and/or displayed. Optionally, outliers of measurement values may be marked and, optionally, filtered out, subject to the operator's (e.g., physician's) approval. Optionally, a graphs relating to plurality of patient and/or other system parameter values may be displayed concurrently, to facilitate the identification of measurement interrelationships (e.g., systolic and diastolic blood pressure measurement values may be displayed concurrently with pulse and weight-values and/or infection-related values of a selected patient). Different patient parameter values may be normalized with respect to each other to allow for comparison.

In some embodiments, the platform may process patient data for a certain patient, or for a multitude of patients (e.g., big data) to perform mathematical (e.g., statistical) analysis and present (e.g. display) results of the performed statistical analysis. Statistical or mathematical analysis may include, for example, an average and/or moving average of patient parameter, a median and/or moving median, plots of moving averages; regression analysis, regression plots; frequency of patient parameter value; Fourier analysis; and/or the like. The platform may for example present a user with a trend (e.g., negative or positive to varying degrees) relating one or more patient parameter values (e.g., weight). For example, a trend or gradient relating to system (e.g., patient) parameter values may be determined based on performing a mathematical differentiation function on the parameter values.

In some embodiments, big data analysis may be performed to implement artificial intelligence (e.g., machine learning) functionalities. For example, data of tens of thousands of peritoneal dialysis patients may be collected, some of which may be used a input training data for the implementation of an AI-based machine learning model (e.g., artificial neural networks) that may be used for determining a state of a patient undergoing, e.g., peritoneal treatment. A patient' state may pertain, for example, to a patient's physical characteristics, for example, for detection of an anomaly in the patient's physical characteristics and characterization (e.g., classification) of the anomaly. Characterization of a physical characteristic may include its classification into peritoneal-related anomaly or not. In some embodiments, classification of a patient's physical characteristics may pertain to its classification as "normal" or "anomalous".

The term "patient data" can include patient initial input data and updated monitoring data. Updated monitoring data is received during patient treatment.

In some embodiments, the user interface allows for entering free text which may be automatically parseable by the dialysis system. The free text may be entered by a patient and/or treating medical professional and parsed for further analysis and diagnostic purposes.

In some embodiments, information relating to past prescriptions and related outcomes, future prescriptions and expected treatment outcome, may be presented to an operator. Optionally, the dialysis system may generate, based on the past prescriptions and the measured outcomes, one or more future prescription alternatives.

Further referring to FIG. 9, a table listing the various exchanges and related parameters may be generated and displayed.

In some embodiments, dialysis system 50 may comprise an authentication and validation engine 1800. Authentication and validation engine 1800 may allow defining various permissions to various operators of the system. For example, system parameters (e.g., treatment prescription) may be configurable by a first operator. However, the permission of the first operator may not allow "signing off" or otherwise give final authorization to actually apply a prescribed treatment. For the purposes, signature of a second operator, different from the first operator, with the necessary permissions may be required.

For example, a nurse may be allowed to enter the parameter values of a patient treatment, yet the signature of a validating supervising physician may be required for allowing applying the selected patient treatment.

Electronic signatures may be given by suitable electronic verification and/or authentication methods. Once final authorization is given, the treatment protocol.

Permission may be managed by an administrator via a permissions matrix. For example, a given system parameter value may be associated with various levels of permission regarding "read", "create", "modify", "delete", and "confirm". A permission may be defined by "grant" or "denied". For example, a certain user may only be allowed to read or view certain values, whereas another user may also be granted the possibility to "modify" and "confirm" values.

Reference is now made to FIG. 11, illustrating a process for providing user(s) with information associated with at least one patient undergoing a dialysis treatment using a dialysis system or device, according to some embodiments. This process may include:

receiving, for the at least one patient of a plurality of patients (e.g., for each patient), patient initial input data, the patient initial input data being descriptive of physical information of the respective patient (block 11111;

analyzing the initial input data, to determine an initial risk level of the respective patient (block 11112);

receiving monitoring data of the respective patient, the monitoring data being indicative of the dialysis treatment of the respective patient (block 11113);

analyzing the patient's initial input data and the monitoring data to: (i) identify one or more anomalous physical characteristics of the respective patient; (ii) determine whether at least one of the identified one or more anomalous physical characteristics of the respective patient is related to the dialysis treatment; and (iii) determine, based on results of the analysis of the initial input data and monitoring data of the respective patient, an updated risk level of the respective patient (block 11114); and displaying, to the at least one user, patient output information indicative at least of: the updated risk level of the respective patient, identified one or more anomalous physical characteristics that are related to the dialysis treatment (block 11115).

The above process may be performed using a CIP such as CIP 1000, a dialysis system/device communicative with the CIP and optionally also one or more external measuring devices, for measuring the patient's physical condition before and/or during the patient's dialysis treatment (such as a thermometer, a blood pressure detector etc.).

Reference is now made to FIG. 12, illustrating a process for providing user(s) with information associated with multiple patients undergoing dialysis treatments within overlapping treatment times, according to some embodiments. This process may include:

receiving initial input data of multiple dialysis treatment patients (block 12211);

receiving display modification data (block 12212), such as, for example, filtering selections form the user;

receiving, in RT or near RT, monitoring data of the at least one of the plurality of patients (e.g., each patient) (block 12213);

performing, for the at least one patient of a plurality of patients (e.g., each patient), in RT or near RT, a personal analysis of the respective patient's input and monitoring data (block 12214) e.g. to determine, for the at least one patient of a plurality of patients (e.g., each patient) his/her updated risk level and/or identify anomalous physical characteristics and whether they are related or not to the dialysis treatment that the patient undergoes;

performing a statistical analysis of all patients, in RT or near RT, based on the patients' personal analysis results (block 12215); and displaying a combined monitoring display (block 12216), the combined monitoring display may be indicative of: (i) results of the statistical analysis (ii) results of the personal analysis of for the at least one patient of a plurality of patients (e.g., each patient); and optionally also indicative of one or more of: initial input data, patients' personal and/or identification data, assigned physician of the at least one patient of a plurality of patients (e.g., each patient), filtering selection, etc.

Further reference is made to FIG. 13.

In some embodiments, a method for providing information (e.g., to a user), wherein the information is associated with at least one patient undergoing dialysis treatment, comprises: receiving patient initial input data, the patient initial input data being descriptive of physical information of the respective patient (block 13100).

In some embodiments, the method may further comprise determining, based on the initial input data, an initial risk level of the respective patient (block 13200).

In some embodiments, the method may include receiving monitoring data of the respective patient, the monitoring data being indicative of the dialysis treatment of the respective patient (block 13300).

In some embodiments, the method may further include determining whether the received updated monitoring data is indicative of an anomalous parameter value of the physical characteristic or not (block 13400).

In some embodiments, the method may include, for an anomalous parameter value, distinguishing (through patient data processing and/or analyzing), for a certain physical characteristic, between an anomalous parameter value that is dialysis-related and an anomalous parameter value that is non-dialysis related (block 13500).

In some embodiments, the method may further include providing an output descriptive of information about the dialysis-related and non-dialysis related anomalous physical characteristics.

In some embodiments, the output may be provided in the form of, for example, labels, colors, widgets, and/or other objects and/or by different display modes (e.g., different colors, blinking, non-blinking, etc.).

Additional Examples

Example 1 includes a computer-implemented platform for providing at least one user with information associated with at least one patient undergoing dialysis treatment, using a dialysis system, the platform comprising:

an I/O device configured to receive, for the at least one patient of a plurality of patients (e.g., for each patient), patient initial input data, the patient initial input data being descriptive of physical information of a respective patient;

an analysis engine configured to perform the following: analyzing the initial input data, to determine an initial risk level of the respective patient; receiving monitoring data of the respective patient, the monitoring data being indicative of the dialysis treatment of the respective patient; analyzing the patient's initial input data and the monitoring data to: identify one or more anomalous physical characteristics of the respective patient; determine whether at least one of the identified one or more anomalous physical characteristics of the respective patient is related to the dialysis treatment; determine, based on results of the analysis of the initial input data and monitoring data of the respective patient, an updated risk level of the respective patient; and a display device configured to display, to the at least one user, patient output information indicative at least of: the updated risk level of the respective patient, identified one or more anomalous physical characteristics that are related to the dialysis treatment.

Example 2 includes the subject matter of example 1 and, optionally, wherein the analysis engine is configured to receive the monitoring data of the respective patient via the I/O device and/or via one or more measuring devices.

Example 3 includes the subject matter of example 2 and, optionally, wherein the one or more measuring devices are configured to detect one or more dialysis parameters values associated with the dialysis treatment of the patient in real time (RT) or near real time (NRT).

Example 4 includes the subject matter of example 3 and, optionally, wherein the one or more dialysis parameters values are indicative of one or more of: patient's body temperature; patient's blood pressure; patient's pulse; used dialysate state; unused dialysate state; dialysis system information; patient's metabolic condition.

Example 5 includes the subject matter of any one or more of examples 1 to 4, and optionally, wherein the initial input data of the respective patient is indicative of one or more of: patient's age, patient's weight, patient's blood pressure, patient's pulse, patient's body mass index (BMI), patient's height, patient's gender, patient's medical history, patient's behavioral history.

Example 6 includes the subject matter of any one or more of examples 1 to 5, optionally, wherein the analysis engine is further configured to identify the one or more anomalous physical characteristics, by comparing at least some of the initial input data with the monitoring data of the respective patient and/or by comparing at least some of the monitoring data of the patient to one or more thresholds defining a normal and abnormal physical state.

Example 7 includes the subject matter of example 6, and optionally, wherein the analysis engine is configured to determine a "hazardous state" of the patient, based on the identified one or more anomalous physical characteristics, wherein the display device is further configured to display a distinctive "alarm display", when a hazardous state is determined.

Example 8 includes the subject matter of example 7, optionally, wherein a hazardous state is indicative of one or more treatment complications.

Example 9 includes the subject matter of example 8, optionally wherein the one or more treatment complications comprise one of the following: peritonitis, dehydration, insufficient ultrafiltration, infection, inflammation, one or more dialysis system operation impediments, or any combination thereof.

Example 10 includes the subject matter of any one or more of examples 7 to 9, optionally wherein the platform further comprises a dialysis control engine, operationally associated with the dialysis system, the dialysis control engine being configured to automatically control operation of the dialysis system, based on results of analysis of the initial input data and the monitoring data of the patient.

Example 11 includes the subject matter of any one or more of examples 1 to 10, optionally, wherein the computer-implemented platform is embeddable in and/or connectable to a computerized processing, data storage and/or interface of the dialysis system.

Example 12 includes the subject matter of any one or more of examples 1 to 11, optionally, wherein the computer-implemented platform further comprises at least one of: a memory, configured to store thereby, for the at least one patient of a plurality of patients (e.g., for each patient) at least one of the following: initial input data, monitoring data and analysis results of each dialysis treatment of the respective patient, data analysis instructions and threshold values, communication related data, medical history of each respective patient, behavioral history of each respective patient; a communication device, configured for communication with the dialysis system and/or other measuring devices and for communication with external data sources and/or data engines, wherein the memory and the communication device are associated with the I/O device, the analysis engine and the display device, for data input, output, communication, storage and analysis.

Example 13 includes the subject matter of any one or more of examples 1 to 12, optionally, wherein the initial and/or updated risk level of the at least one patient of a plurality of patients (e.g., of each patient) is associated with one of several risk-profile groups.

Example 14 includes the subject matter of example 13, optionally, wherein the risk profile groups comprise: high risk, low risk and no-risk.

Example 15 includes the subject matter of any one or more of examples 13 to 14, optionally, wherein the analysis engine is further configured to simultaneously analyze initial input data and monitoring data for a multiplicity of patients undergoing dialysis treatments, and the display device is configured to display, to the at least one user, a combined monitoring display, visually indicative of output information of multiple patients undergoing dialysis treatments.

Example 16 includes the subject matter of example 15, optionally, wherein the combined monitoring display comprises visual display of one or more of the following: a table displaying information of all patients undergoing dialysis treatment, displaying, for the at least one patient of a plurality of patients (e.g., for each patient), patient information indicative of at least one of: patient identification information, professional staff member associated with the respective patient, patient initial input data or part thereof, patient initial and/or updated risk level, patient one or more identified anomalous physical characteristics, patient one or more identified anomalous physical characteristics that are related to the patient's dialysis treatment; updated statistical information indicative of statistics of all patients undergoing dialysis treatment.

Example 17 includes the subject matter of one or more of examples example 15 to 16, optionally, wherein the analysis engine is further configured to analyze initial and monitoring data of multiple patients undergoing a dialysis treatment, to generate updated statistical information indicative of one or more of: the number of patients associated with each risk profile group; the number of patients for whom one or more anomalous physical characteristics have been identified; the number of patients for whom one or more anomalous physical characteristics relating to their dialysis treatment have been identified; wherein the updated statistical information is displayable by the display device via the combined monitoring display.

Example 18 includes the subject matter of example 17, optionally, wherein the visual display of the number of patients associated with each risk profile group is carried out via one or more of: pie chart display, bar chart display, numbers display indicative of actual number of patients in each risk profile group, histogram display.

Example 19 includes the subject matter of any one or more of examples 16 to 18, optionally, wherein the combined monitoring display is configured to enable visual distinction of patients identified with one or more anomalous physical characteristics that are related to their dialysis treatment.

Example 20 includes the subject matter of example any one or more of examples 1 to 19, optionally, wherein the dialysis treatment is one of: peritoneal dialysis, hemodialysis.

Example 21 is a method for providing at least one user with information associated with at least one patient undergoing dialysis treatment, using a dialysis system, the method comprising:

receiving, for the at least one patient of a plurality of patients (e.g., for each patient), patient initial input data, the patient initial input data being descriptive of physical information of the respective patient;

analyzing the initial input data, to determine an initial risk level of the respective patient;

receiving monitoring data of the respective patient, the monitoring data being indicative of the dialysis treatment of the respective patient;

analyzing the patient's initial input data and the monitoring data to: identify one or more anomalous physical characteristics of the respective patient; determine whether at least one of the identified one or more anomalous physical characteristics of the respective patient is related to the dialysis treatment; determine, based on results of the analysis of the initial input data and monitoring data of the respective patient, an updated risk level of the respective patient; and displaying, to the at least one user, patient output information indicative at least of: the updated risk level of the respective patient, identified one or more anomalous physical characteristics that are related to the dialysis treatment.

Example 22 includes the subject matter of example 21, optionally, wherein at least part of the monitoring data of the respective patient is received via one or more measuring devices, each measuring device being configured to detect one or more dialysis parameters values associated with the dialysis treatment of the patient in real time (RT) or near real time (NRT).

Example 23 includes the subject matter of example 22, optionally, wherein the one or more dialysis parameters values are indicative of one or more of: patient's body temperature; patient's blood pressure; patient's pulse; used dialysate state; unused dialysate state; dialysis system information; patient's metabolic condition.

Example 24 includes the subject matter of any one or more of example 21 to 23, optionally, wherein the initial input data of the respective patient is indicative of one or more of: patient's age, patient's weight, patient's blood pressure, patient's pulse, patient's body mass index (BMI), patient's height, patient's gender, patient's medical history, patient's behavioral history.

Example 25 includes the subject matter of any one or more of examples 21 to 24, optionally, wherein the identification of one or more anomalous physical characteristics, is carried out by comparing at least some of the initial input data with the monitoring data of the respective patient and/or by comparing at least some of the monitoring data of the patient to one or more thresholds defining a normal and abnormal physical state.

Example 26 includes the subject matter of example 25 optionally, wherein the method further comprises determining a "hazardous state" of the respective patient, based on the identified one or more anomalous physical characteristics, and displaying a distinctive "alarm display", when a hazardous state is determined.

Example 27 includes the subject matter of example 26, optionally, wherein a hazardous state is indicative of one or more treatment complications.

Example 28 includes the subject matter of example 27, optionally, wherein the one or more treatment complications comprise one of the following: peritonitis, dehydration, insufficient ultrafiltration, infection, inflammation, one or more dialysis system operation impediments, or any combination thereof.

Example 29 includes the subject matter of any one or more of examples 21 to 28, optionally, wherein the method further comprises automatically controlling operation of the dialysis system, based on results of analysis of the initial input data and the monitoring data of the patient.

Example 30 includes the subject matter of any one or more of examples 21 to 29, optionally, wherein the initial and/or updated risk level for the at least one patient of a plurality of patients (e.g., for each patient), is associated with one of several risk-profile groups.

Example 31 includes the subject matter of example 30, optionally, wherein the risk profile groups comprise: high risk, low risk and no-risk.

Example 32 includes the subject matter of any one or more of examples 30 to 31, optionally, wherein the method further comprises simultaneously analyzing initial input data and monitoring data of a multiplicity of patients undergoing dialysis treatments, and displaying, to the at least one user, a combined monitoring display, visually indicative of output information of multiple patients undergoing dialysis treatments.

Example 33 includes the subject matter of example 32, optionally, wherein the combined monitoring display comprises visual display of: a table displaying information of all patients undergoing dialysis treatment, displaying, for the at least one patient of a plurality of patients (e.g., for each patient), patient information indicative of at least one of: patient identification information, professional staff member associated with the respective patient, patient initial input data or part thereof, patient initial and/or updated risk level, patient one or more identified anomalous physical characteristics, patient one or more identified anomalous physical characteristics that are related to the patient's dialysis treatment; updated statistical information indicative of statistics of all patients undergoing dialysis treatment.

Example 34 includes the subject matter of examples 32 to 33, optionally, wherein the method further comprises generating updated statistical information indicative of one or more of: the number of patients associated with each risk profile group; the number of patients for whom one or more anomalous physical characteristics have been identified; the number of patients for whom one or more anomalous physical characteristics relating to their dialysis treatment have been identified, wherein the updated statistical information is displayable via the combined monitoring display.

Example 35 includes the subject matter of example 34, optionally, wherein the visual display of the number of patients associated with each risk profile group is carried out via one or more of: pie chart display, bar chart display, numbers display indicative of actual number of patients in each risk profile group, histogram display.

Example 36 includes the subject matter of any one or more of examples 32 to 35, optionally, wherein the combined monitoring display is configured to enable visual distinction of patients identified with one or more anomalous physical characteristics that are related to their dialysis treatment.

Example 37 includes the subject matter of any one or more of examples 21 to 36, optionally, wherein the dialysis treatment is one of: peritoneal dialysis, hemodialysis.

Example 38, includes the subject matter of any one or more of examples 21 to 37 and, optionally, wherein the determining of the updated risk level of the patient comprises deciding to change the patient's risk level only upon identification of anomalous physical characteristics that are directly related to the dialysis treatment that the respective patient undergoes.

Example 39 pertains to a computer-implemented platform for providing at least one user with information associated with at least one patient undergoing dialysis treatment, using a dialysis system, the platform comprising:

an I/O device configured to receive, for the at least one patient of a plurality of patients (e.g., for each patient), patient initial input data, the patient initial input data being descriptive of physical information of a respective patient;

an analysis engine configured to perform the following:

analyzing the patient initial input data, to determine an initial risk level of the at least one patient;

receiving updated monitoring data of the respective patient, the updated monitoring data being received during a dialysis treatment of the at least one patient;

analyzing the received initial patient input data and the updated monitoring data to:

determine one or more anomalous physical characteristics for the at least one patient, respectively;

determine whether at least one of the identified one or more anomalous physical characteristics of the at least one patient is related to the dialysis treatment or not;

update a risk level of the at least one patient when the anomalous physical characteristics is related to the dialysis treatment;

a display device configured to concurrently display, to the at least one user:

an updated risk level of the at least one patient and information about the associated dialysis-related anomalous physical characteristic; and information about non-dialysis related anomalous physical characteristics.

Example 40 includes the subject matter of example 39 and, optionally, wherein the analyzing further comprises determining whether a non-dialysis related anomalous physical characteristic has a potential to adversely affect or is presently adversely affecting a dialysis-related physical characteristic or not.

Example 41 includes the subject matter of examples 39 or 40 and, optionally, wherein the analyzing further comprises determining whether a dialysis related anomalous physical characteristic has the potential to adversely affect or is presently adversely affecting a non-dialysis related physical characteristic or not.

Example 42 includes the subject matter of any one or more of the Examples 39 to 41 and, optionally, wherein the display device is configurable to selectively display or not display information about non-dialysis related anomalous physical characteristics.

Example 43 includes the subject matter of any one or more of the Examples 39 to 42 and, optionally, wherein the display device is configurable to selectively display or not display information about dialysis related anomalous physical characteristics.

Example 44 includes the subject matter of any one or more of the Examples 39 to 43 and, optionally, wherein the analyzing of the received initial input data and the updated monitoring data includes classifying detected anomalous characteristics into one of the following:

non-dialysis-related physical characteristic that does adversely affect dialysis related physical characteristics; and dialysis-related physical characteristic that does adversely affect non-dialysis related physical characteristics.

Example 45 includes the subject matter of any one or more of the Examples 39 to 44 and, optionally, wherein the analyzing of the received initial input data and the updated monitoring data includes classifying detected anomalous characteristics into one of the following:

dialysis-related physical characteristics that does adversely affect.

Example 46 includes the subject matter of any one or more of the Examples 39 to 45 and, optionally, wherein an anomalous physical characteristics is defined as related to the dialysis treatment, when the respective anomalous physical characteristics puts the respective patient at risk of developing one or more dialysis treatment related complications.

Example 47 includes the subject matter of any one or more of the Examples 39 to 46 and, optionally, wherein the analysis engine is configured to receive the monitoring data of the respective patient via the I/O device and/or via one or more measuring devices.

Example 48 includes the subject matter of any one or more of the Examples 39 to 47 and, optionally, wherein the one or more measuring devices are configured to detect one or more dialysis parameters values associated with the dialysis treatment of the patient in real time (RT) or near real time (NRT).

Example 49 includes the subject matter of any one or more of the Examples 39 to 48 and, optionally, wherein the one or more dialysis parameters values are indicative of one or more of: patient's body temperature; patient's blood pressure; patient's pulse; used dialysate state; unused dialysate state; dialysis system information; patient's metabolic condition.

Example 50 includes the subject matter of any one or more of the Examples 39 to 49 and, optionally, wherein the initial input data of the respective patient is indicative of one or more of: patient's age, patient's weight, patient's blood pressure, patient's pulse, patient's body mass index (BMI), patient's height, patient's gender, patient's medical history, patient's behavioral history.

Example 51 includes the subject matter of any one or more of the Examples 39 to and, optionally, wherein the analysis engine is further configured to identify the one or more anomalous physical characteristics, by comparing at least some of the initial input data with the monitoring data of the respective patient and/or by comparing at least some of the monitoring data of the patient to one or more thresholds defining a normal and abnormal physical state.

Example 52 includes the subject matter of any one or more of the Examples 39 to 51 and, optionally, wherein the analysis engine is configured to determine a "hazardous state" of the patient, based on the identified one or more anomalous physical characteristics, wherein the display device is further configured to display a distinctive "alarm display", when a hazardous state is determined.

Example 53 includes the subject matter of Example 52 and, optionally, wherein a hazardous state is indicative of one or more dialysis treatment complications.

Example 54 includes the subject matter of any one or more of the Examples 39 to 53 and, optionally, wherein the one or more treatment complications comprise one of the following: peritonitis, dehydration, insufficient ultrafiltration, infection, inflammation, one or more dialysis system operation impediments, or any combination thereof.

Example 55 includes the subject matter of any one or more of the Examples 39 to 54 and, optionally, further comprising a dialysis control engine, operationally associated with the dialysis system, the dialysis control engine being configured to automatically control operation of the dialysis system, based on results of analysis of the initial input data and the monitoring data of the patient.

Example 56 includes the subject matter of any one or more of the Examples 39 to and, optionally, being embeddable in and/or connectable to a computerized processing, data storage and/or interface of the dialysis system.

Example 57 includes the subject matter of any one or more of the Examples 39 to 56 and, optionally, further comprising at least one of: a memory, configured to store thereby, for the at least one patient of a plurality of patients (e.g., for each patient), at least one of the following: initial input data, monitoring data and analysis results of each dialysis treatment of the respective patient, data analysis instructions and threshold values, communication related data, medical history of each respective patient, behavioral history of each respective patient; a communication device, configured for communication with the dialysis system and/or other measuring devices and for communication with external data sources and/or data engines, wherein the memory and the communication device are associated with the I/O device, the analysis engine and the display device, for data input, output, communication, storage and analysis.

Example 58 includes the subject matter of any one or more the examples 39 to 57 and, optionally, wherein the initial and/or updated risk level of the at least one patient of a plurality of patients (e.g., of each patient) is associated with one of several risk-profile groups.

Example 59 includes the subject matter of any one or more of the examples 39 to 58 and, optionally, wherein the risk profile groups comprise: high risk, medium risk, low risk and no-risk.

Example 60 includes the subject matter of any one or more of the Examples 39 to 59 and, optionally, wherein the analysis engine is further configured to simultaneously analyze initial input data and monitoring data for a multiplicity of patients undergoing dialysis treatments, and the display device is configured to display, to the at least one user, a combined monitoring display, visually indicative of output information of multiple patients undergoing dialysis treatments.

Example 61 includes the subject matter of Example 59 and, optionally, wherein the combined monitoring display comprises visual display of one or more of the following:

a table displaying information of all patients undergoing dialysis treatment, displaying, for the at least one patient of a plurality of patients (e.g., for each patient), patient information indicative of at least one of: patient identification information, professional staff member associated with the respective patient, patient initial input data or part thereof, patient initial and/or updated risk level, patient one or more identified anomalous physical characteristics, patient one or more identified anomalous physical characteristics that are related to the patient's dialysis treatment;

updated statistical information indicative of statistics of all patients undergoing dialysis treatment.

Example 62 includes the subject matter of example 60 or 61 and, optionally, wherein the analysis engine is further configured to analyze initial and monitoring data of multiple patients undergoing a dialysis treatment, to generate updated statistical information indicative of one or more of:

the number of patients associated with each risk profile group;

the number of patients for whom one or more anomalous physical characteristics have been identified;

the number of patients for whom one or more anomalous physical characteristics relating to their dialysis treatment have been identified;

wherein the updated statistical information is displayable by the display device via the combined monitoring display.

Example 63 includes the subject matter of Example 62 and, optionally, wherein the visual display of the number of patients associated with each risk profile group is carried out via one or more of: pie chart display, bar chart display, numbers display indicative of actual number of patients in each risk profile group, histogram display.

Example 64 includes the subject matter of any one or more of Examples 60 to 63 and, optionally, wherein the combined monitoring display is configured to enable visual distinction of patients identified with one or more anomalous physical characteristics that are related to their dialysis treatment.

Example 65 includes the subject matter of any one or more of the examples 39 to 64 and, optionally, wherein the dialysis treatment is one of: peritoneal dialysis, hemodialysis Example 66 includes the subject matter of any one or more of the examples 39 to 65 and, optionally, wherein an anomalous characteristic that is not related to peritoneal dialysis pertains to a viral infection.

Example 67 includes a method for providing at least one user with information associated with at least one patient undergoing dialysis treatment, using a dialysis system, the method comprising:

receiving, for the at least one patient of a plurality of patients (e.g., for each patient), patient initial input data, the patient initial input data being descriptive of physical information of the respective patient;

analyzing the initial input data, to determine an initial risk level of the respective patient;

receiving monitoring data of the respective patient, the monitoring data being indicative of the dialysis treatment of the respective patient;

analyzing the patient's initial input data and monitoring data to determine one or more anomalous physical characteristics for the at least one patient, respectively;

determine whether at least one of the identified one or more anomalous physical characteristics of the at least one patient is related to the dialysis treatment or not;

update a risk level of the at least one patient when the anomalous physical characteristics is related to the dialysis treatment; and when applicable, displaying, to the at least one user:

an updated risk level of the at least one patient and information about the associated dialysis-related anomalous physical characteristic; and information about non-dialysis related anomalous physical characteristics.

Example 68 includes the subject matter of example 67 and, optionally, configuring a display device to selectively display or not display information about non-dialysis related anomalous physical characteristics.

Example 69 includes the subject matter of examples 67 and/or 68 and, optionally, wherein the analyzing of the received initial input data and the updated monitoring data includes classifying detected anomalous characteristics into one of the following: dialysis-related and non-dialysis related anomalous physical characteristics.

Example 70 includes the subject matter of any one or more of Examples 67 to 69, wherein an anomalous physical characteristics is defined as related to the dialysis treatment, when the respective anomalous physical characteristics puts the respective patient at risk of developing one or more dialysis treatment related complications.

Example 71 includes the subject matter of any one or more of the examples 67 to 70 and, optionally, wherein at least part of the monitoring data of the respective patient is received via one or more measuring devices, each measuring device being configured to detect one or more dialysis parameters values associated with the dialysis treatment of the patient in real time (RT) or near real time (NRT).

Example 72 includes the subject matter of any one or more of the examples 67 to 71 and, optionally, wherein the one or more dialysis parameters values are indicative of one or more of: patient's body temperature; patient's blood pressure; patient's pulse; used dialysate state; unused dialysate state; dialysis system information; patient's metabolic condition.

Example 73 includes the subject matter of any one or more of examples 67 to 72, wherein the initial input data of the respective patient is indicative of one or more of: patient's age, patient's weight, patient's blood pressure, patient's pulse, patient's body mass index (BMI), patient's height, patient's gender, patient's medical history, patient's behavioral history.

Example 74 includes the subject matter of any one or more of the examples 67 to 73 and, optionally, wherein the identification of one or more anomalous physical characteristics, is carried out by comparing at least some of the initial input data with the monitoring data of the respective patient and/or by comparing at least some of the monitoring data of the patient to one or more thresholds defining a normal and abnormal physical state.

Example 75 includes the subject matter of example 67 to 74 and, optionally, further comprising determining a "hazardous state" of the respective patient, based on the identified one or more anomalous physical characteristics, and displaying a distinctive "alarm display", when a hazardous state is determined.

Example 76 includes the subject matter of Example 75 and, optionally, wherein a hazardous state is indicative of one or more treatment complications.

Example 77 includes the subject matter of Example 76 and, optionally, wherein the one or more treatment complications comprise one of the following: peritonitis, dehydration, insufficient ultrafiltration, infection, inflammation, one or more dialysis system operation impediments, or any combination thereof.

Example 78 includes the subject matter of any one or more of the Examples 67 to 77 and, optionally, further comprising automatically controlling operation of the dialysis system, based on results of analysis of the initial input data and the monitoring data of the patient.

Example 79 includes the subject matter of any one or more of examples 67 to 78 and, optionally, wherein the initial and/or updated risk level of the at least one patient of a plurality of patients (e.g., of each patient), is associated with one of several risk-profile groups.

Example 80 includes the subject matter of Example 79 and, optionally, wherein the risk profile groups comprise: high risk, low risk and no-risk.

Example 81 includes the subject matter of any one or more of the Examples 67 to 80 and, optionally, further comprising simultaneously analyzing initial input data and monitoring data of a multiplicity of patients undergoing dialysis treatments, and displaying, to the at least one user, a combined monitoring display, visually indicative of output information of multiple patients undergoing dialysis treatments.

Example 82 includes the subject matter of example 81 and, optionally, wherein the combined monitoring display comprises visual display of:

a table displaying information of all patients undergoing dialysis treatment, displaying, e.g., for the at least one patient of a plurality of patients (e.g., for each patient), patient information indicative of at least one of: patient identification information, professional staff member associated with the respective patient, patient initial input data or part thereof, patient initial and/or updated risk level, patient one or more identified anomalous physical characteristics, patient one or more identified anomalous physical characteristics that are related to the patient's dialysis treatment;

updated statistical information indicative of statistics of all patients undergoing dialysis treatment.

Example 83 includes the subject matter of any one or more of the Examples 81 and/or 82 and, optionally, further comprising generating updated statistical information indicative of one or more of:

the number of patients associated with each risk profile group;

the number of patients for whom one or more anomalous physical characteristics have been identified;

the number of patients for whom one or more anomalous physical characteristics relating to their dialysis treatment have been identified;

wherein the updated statistical information is displayable via the combined monitoring display.

Example 84 includes the subject matter of Example 83 and, optionally, wherein the visual display of the number of patients associated with each risk profile group is carried out via one or more of: pie chart display, bar chart display, numbers display indicative of actual number of patients in each risk profile group, histogram display.

Example 85 includes the subject matter of any one or more of examples 67 to 84 and, Optionally, wherein the combined monitoring display is configured to enable visual distinction of patients identified with one or more anomalous physical characteristics that are related to their dialysis treatment.

Example 86 includes the subject matter of any one or more of Examples 67 to 85 and, optionally wherein the dialysis treatment is one of: peritoneal dialysis, hemodialysis.

Example 87 includes the subject matter of any one or more of the Examples 67 to 86 and, optionally, wherein the determining of the updated risk level of the patient comprises deciding to change the patient's risk level only upon identification of anomalous physical characteristics that are directly related to the dialysis treatment that the respective patient undergoes.

In some examples, a computer-implemented platform for providing at least one user with information associated with at least one patient undergoing dialysis treatment, using a dialysis system, may comprise an I/O device configured to receive patient initial input data relating to at least one patient, the patient initial input data being descriptive of a physical characteristic of the at least one patient; and wherein the I/O device is further configured to receive updated monitoring data of the patient, the updated monitoring data being received during a dialysis treatment of the at least one patient; an analysis engine configured to: determine whether the received updated monitoring data is indicative of an anomalous parameter value of the physical characteristic or not; and, when the received updated monitoring data is indicative of an anomalous parameter value or for received updated monitoring data that is indicative of an anomalous parameter value: distinguish (e.g., through patient data processing and/or analyzing), for a certain physical characteristic, between an anomalous parameter value that is dialysis-related and an anomalous parameter value that is non-dialysis related; and, optionally, display and/or otherwise produce an output (e.g., in association with information) about dialysis-related and/or non-dialysis related anomalous physical characteristics.

The output may include an object and/or pertain to different display modes, to allow the user the distinguish between information about dialysis-related and/or non-dialysis related anomalous physical characteristics.

It is noted that the values of the first and the second anomalous parameter value may be identical or different from each other. However, the system is configured to determine (e.g., classify) whether the anomalous parameter value is dialysis-related or not dialysis related.

In some examples, the analysis engine is configured to determine, based on the received initial patient data, a risk level of the at least one patient for suffering from dialysis treatment complications; and configured to update the risk level to an increased risk level when the analysis engine determines that the anomalous physical characteristics is not related to the dialysis treatment.

In some examples, the anomalous physical characteristic is increased patient weight, wherein the analysis engine is configured to monitor ultrafiltration parameter values and bowl activity to determine whether increased patient weight is due to food intake, digestive disorder, insufficient ultrafiltration, or both.

In some examples, the analysis engine provides an output to the dialysis system to increase a relative amount of osmotic agent in a peritoneal dialysis solution of the dialysis system.

In some examples, the I/O device comprises a camera for determining, based on an indentation in patient's tissue, whether an increase in weight is at least partially due to edema caused by insufficient ultrafiltration.

In some examples, the analysis engine is configured to determine a magnitude of a physical parameter that contributes non-dialysis-related anomalous physical characteristic and further configured to determine, for the same physical parameter, a magnitude that contributes to dialysis-related anomalous physical characteristic.

In some examples, the analysis engine is configured to determine a first amount of an increase in weight that is caused by food intake and further a second amount of an increase in weight that is caused by dialysis.

In some examples, the analysis engine is configured to monitor operational parameters values of the dialysis system for detecting one or more dialysis system related impediments.

In some examples, the one or more dialysis system related impediments include: improper catheter placement; catheter leakage; catheter blockage; dialysis system pump malfunction; dialysate turbidity state; or any combination of the aforesaid.

In some examples, a method for providing at least one user with information associated with at least one patient undergoing dialysis treatment, using a dialysis system, comprises:

receiving, for the at least one patient of a plurality of patients (e.g., for each patient), patient initial input data, the patient initial input data being descriptive of physical information of the respective patient; determining, based on the initial input data, an initial risk level of the respective patient;

receiving monitoring data of the respective patient, the monitoring data being indicative of the dialysis treatment of the respective patient;

determining whether the received updated monitoring data is indicative of an anomalous parameter value of the physical characteristic or not;

and, when the received updated monitoring is indicative of an anomalous parameter value:

distinguishing (e.g., (through patient data processing and/or analyzing), for a certain physical characteristic, between an anomalous parameter value that is dialysis-related and an anomalous parameter values that is non-dialysis related; and, optionally, provide an output which provides information about the dialysis-related and non-dialysis related anomalous physical characteristics.

In some embodiments, the output may include annotations, labels, colors, and/or other objects and/or display modes for providing information about the dialysis-related and non-dialysis related anomalous physical characteristics. In some examples, the output may include displayed labels and/or other objects in association with information about dialysis-related and non-dialysis related anomalous physical characteristics.

Any digital computer system, unit, device, module and/or engine exemplified herein can be configured or otherwise programmed to implement a method disclosed herein, and to the extent that the system, module and/or engine is configured to implement such a method, it is within the scope and spirit of the disclosure. Once the system, module and/or engine are programmed to perform particular functions pursuant to computer readable and executable instructions from program software that implements a method disclosed herein, it in effect becomes a special purpose computer particular to embodiments of the method disclosed herein. The methods and/or processes disclosed herein may be implemented as a computer program product that may be tangibly embodied in an information carrier including, for example, in a non-transitory tangible computer-readable and/or non-transitory tangible machine-readable storage device. The computer program product may directly loadable into an internal memory of a digital computer, comprising software code portions for performing the methods and/or processes as disclosed herein.

Additionally or alternatively, the methods and/or processes disclosed herein may be implemented as a computer program that may be intangibly embodied by a computer readable signal medium. A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a non-transitory computer or machine-readable storage device and that can communicate, propagate, or transport a program for use by or in connection with apparatuses, systems, platforms, methods, operations and/or processes discussed herein.

The terms "non-transitory computer-readable storage device" and "non-transitory machine-readable storage device" encompasses distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by one or more communication networks.

These computer readable and executable instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable and executable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable and executable instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The terms "engine" and/or "module" may comprise one or more computer modules, wherein a module may be a self-contained hardware and/or software component (e.g., circuitry) that interfaces with a larger system. A module may comprise a machine or machines executable instructions. A module may be embodied by a circuit or a controller programmed to cause the system to implement the method, process and/or operation as disclosed herein. For example, a module may be implemented as a hardware circuit comprising, e.g., custom VLSI circuits or gate arrays, an Application-specific integrated circuit (ASIC), off-the-shelf semiconductors such as logic chips, transistors, and/or other discrete components. A module may also be implemented in programmable hardware devices such as field programmable gate arrays, programmable array logic, programmable logic devices and/or the like.

In the discussion, unless otherwise stated, adjectives such as "substantially" and "about" that modify a condition or relationship characteristic of a feature or features of an embodiment of the invention, are to be understood to mean that the condition or characteristic is defined to within tolerances that are acceptable for operation of the embodiment for an application for which it is intended.

Unless otherwise specified, the terms "substantially", "about" and/or "close" with respect to a magnitude or a numerical value may imply to be within an inclusive range of −10% to +10% of the respective magnitude or value.

It is important to note that the method may include is not limited to those diagrams or to the corresponding descriptions. For example, the method may include additional or even fewer processes or operations in comparison to what is described in the figures. In addition, embodiments of the method are not necessarily limited to the chronological order as illustrated and described herein.

Discussions herein utilizing terms such as, for example, "processing", "computing", "calculating", "determining", "establishing", "analyzing", "checking", "estimating", "deriving", "selecting", "inferring" or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes. The term determining may, where applicable, also refer to "heuristically determining".

It should be noted that where an embodiment refers to a condition of "above a threshold", this should not be construed as excluding an embodiment referring to a condition of "equal or above a threshold". Analogously, where an embodiment refers to a condition "below a threshold", this should not be construed as excluding an embodiment referring to a condition "equal or below a threshold". It is clear that should a condition be interpreted as being fulfilled if the value of a given parameter is above a threshold, then the same condition is considered as not being fulfilled if the value of the given parameter is equal or below the given threshold. Conversely, should a condition be interpreted as being fulfilled if the value of a given parameter is equal or above a threshold, then the same condition is considered as not being fulfilled if the value of the given parameter is below (and only below) the given threshold.

It should be understood that where the claims or specification refer to "a" or "an" element and/or feature, such reference is not to be construed as there being only one of that element. Hence, reference to "an element" or "at least one element" for instance may also encompass "one or more elements".

Terms used in the singular shall also include the plural, except where expressly otherwise stated or where the context otherwise requires.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Unless otherwise stated, the use of the expression "and/or" between the last two members of a list of options for selection indicates that a selection of one or more of the listed options is appropriate and may be made. Further, the use of the expression "and/or" may be used interchangeably with the expressions "at least one of the following", "any one of the following" or "one or more of the following", followed by a listing of the various options.

It is appreciated that certain features of the invention, which are, for clarity, described in the context of separate embodiments or example, may also be provided in combination in a single embodiment. Conversely, various features of the invention, which are, for brevity, described in the context of a single embodiment, example and/or option, may also be provided separately or in any suitable sub-combination or as suitable in any other described embodiment, example or option of the invention. Certain features described in the context of various embodiments, examples and/or optional implementation are not to be considered essential features of those embodiments, unless the embodiment, example and/or optional implementation is inoperative without those elements.

It is noted that the terms "in some embodiments", "according to some embodiments", "according to some embodiments of the invention", "for example", "e.g.", "for instance" and "optionally" may herein be used interchangeably.

The number of elements shown in the Figures should by no means be construed as limiting and is for illustrative purposes only.

It is noted that the terms "operable to" can encompass the meaning of the term "modified or configured to". In other words, a machine "operable to" perform a task can in some embodiments, embrace a mere capability (e.g., "modified") to perform the function and, in some other embodiments, a machine that is actually made (e.g., "configured") to perform the function.

Throughout this application, various embodiments may be presented in and/or relate to a range format. It should be understood that the description in range format is merely for convenience and brevity and should not be construed as an inflexible limitation on the scope of the embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

While the invention has been described with respect to a limited number of embodiments, these should not be construed as limitations on the scope of the invention, but rather as exemplifications of some of the embodiments.

What is claimed is:

1. A computer-implemented platform for providing information associated with at least one patient undergoing dialysis treatment, using a dialysis system, the platform comprising:

an I/O device configured to receive patient initial input data relating to at least one patient, the patient initial input data being descriptive of a physical characteristic of the at least one patient; and wherein the I/O device is further configured to receive, from at least one sensor of the dialysis system, updated monitoring data of the patient, the updated monitoring data being received during a dialysis treatment of the at least one patient;

processor; and a memory configured to store software executable by the processor to enable performing the following, in real-time or substantially in real-time, at least with respect to the received updated monitoring data:

determining whether the received updated monitoring data is indicative of an anomalous parameter value of the physical characteristic or not;

and, for received updated monitoring data that is indicative of an anomalous parameter value:

distinguishing, for a certain physical characteristic, between an anomalous parameter value that is dialysis-related and an anomalous parameter value that is non-dialysis related; and providing an output to indicate which anomalous parameter value is dialysis-related and which not, and providing a treatment step with respect to identifying an anomalous parameter value as being dialysis-related, wherein the treatment step is provided in real-time or near real-time with respect to the identifying.

2. The computer-implemented platform of claim 1, wherein providing an output comprises displaying one or more objects in association with information about dialysis-related and non-dialysis related anomalous physical characteristics.

3. The computer-implemented platform of claim 1, wherein the dialysis system is further configured to perform the following:

determining, based on the received initial patient data, a risk level of the at least one patient for suffering from dialysis treatment complications; and updating the risk level to an increased risk level when the dialysis system determines that the anomalous physical characteristics is not related to the dialysis treatment.

4. The computer-implemented platform of claim 1, wherein the anomalous physical characteristic is increased patient weight; and wherein the dialysis system is configured to monitor ultrafiltration parameter values and bowl activity to determine whether increased patient weight is due to food intake, digestive disorder, insufficient ultrafiltration, or both.

5. The computer-implemented platform of claim 1, wherein the I/O device comprises a camera for determining, based on an indentation in patient's tissue, whether an increase in weight is at least partially due to edema caused by insufficient ultrafiltration.

6. The computer-implemented platform of claim 1, wherein the dialysis system is configured to determine a first amount of an increase in weight that is caused by food intake and further a second amount of an increase in weight that is caused by dialysis.

7. The computer-implemented platform of claim 1, further configured to monitor operational parameters values of the dialysis system for detecting one or more dialysis system related impediments.

8. The computer-implemented platform of claim 1, wherein the dialysis system is further configured to determine whether a non-dialysis related anomalous physical characteristic has a potential to adversely affect or is presently adversely affecting a dialysis-related physical characteristic or not.

9. The computer-implemented platform of claim 1, wherein the dialysis system is further configured to determine whether a dialysis related anomalous physical characteristic has a potential to adversely affect or is presently adversely affecting a non-dialysis related physical characteristic or not.

10. The computer-implemented platform of claim 1, wherein the dialysis system is configured to classify detected anomalous characteristics into one of the following:

non-dialysis-related physical characteristic that does adversely affect dialysis related physical characteristics; and dialysis-related physical characteristic that does adversely affect non-dialysis related physical characteristics.

11. The computer-implemented platform of claim 1, wherein an anomalous physical characteristics is defined as related to the dialysis treatment, when the respective anomalous physical characteristics puts the respective patient at risk of developing one or more dialysis treatment related complications.

12. The computer-implemented platform of claim 1, configured to determine, based on measuring values relating to operating system parameters of the dialysis system, a level of adherence of a patient undergoing a recommended treatment regime.

13. The computer-implemented platform of claim 3, wherein the dialysis system is further configured to identify the one or more anomalous physical characteristics, by comparing at least some of the initial input data with the monitoring data of the respective patient and/or by comparing at least some of the monitoring data of the patient to one or more thresholds defining a normal and abnormal physical state.

14. The computer-implemented platform of claim 1, wherein the dialysis system is further configured to simultaneously analyze initial input data and monitoring data for a multiplicity of patients undergoing dialysis treatments, and a display device is configured to display, to the at least one user, a combined monitoring display, visually indicative of output information of multiple patients undergoing dialysis treatments.

15. The computer-implemented platform of claim 1, wherein the dialysis system is configured to predict, based on patient data received at the platform during a recent monitored time interval, an onset of complications related to peritoneal patient treatment and predict an estimated future time stamp or future time interval of the onset of such complications.

16. A method for providing information associated with at least one patient undergoing dialysis treatment, using a dialysis system, comprises:

receiving for the at least one patient, patient initial input data, the patient initial input data being descriptive of physical information of the respective at least one patient;

determining, based on the initial input data, an initial risk level of the respective patient;

receiving monitoring data of the respective patient in real time or near real time, the monitoring data being indicative of the dialysis treatment of the respective patient;

processing, in real-time or substantially in real-time, the patient initial input data, the initial risk level of the respective patient and the monitoring data of the respective patient;

determining, in real-time or substantially in real-time at least with respect to the receiving of the received monitoring data, whether the received updated monitoring data is indicative of an anomalous parameter value of the physical characteristic or not;

distinguishing, for a certain physical characteristic, between a received updated monitoring data that is indicative of an anomalous parameter value that is dialysis-related and an anomalous parameter value that is non-dialysis related;

providing an output to indicate which anomalous parameter value is dialysis-related and which not; and providing a treatment step with respect to detecting an anomalous parameter value that is dialysis-related, wherein the treatment step is provided in real-time or near real-time with respect to the detection of the dialysis-related anomaly.

17. The method of claim 16, wherein providing the output comprises displaying one or more objects in association with information about dialysis-related and non-dialysis related anomalous physical characteristics.

18. The method of claim 16, configuring a display device to selectively display or not display information about non-dialysis related anomalous physical characteristics.

19. The method of claim 16, wherein at least part of the monitoring data of the respective patient is received via one or more measuring devices, each measuring device being configured to detect one or more dialysis parameters values associated with the dialysis treatment of the patient in real time (RT) or near real time (NRT).

20. The method of claim 16, wherein the determining of the updated risk level of the patient comprises deciding to change the patient's risk level only upon identification of anomalous physical characteristics that are directly related to the dialysis treatment that the respective patient undergoes.

\* \* \* \* \*